United States Patent
Wen et al.

(10) Patent No.: US 8,496,963 B2
(45) Date of Patent: *Jul. 30, 2013

(54) ORAL FORMULATIONS OF GLYCYL-2-METHYLPROLYL-GLUTAMATE

(76) Inventors: Jingyuan Wen, Mt. Eden (NZ); Gregory Brian Thomas, Kingsley (AU); Mike John Bickerdike, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/471,150

(22) Filed: May 14, 2012

(65) Prior Publication Data

US 2012/0277167 A1    Nov. 1, 2012

Related U.S. Application Data

(63) Continuation of application No. 13/026,787, filed on Feb. 14, 2011, now Pat. No. 8,178,125, which is a continuation of application No. 12/283,684, filed on Sep. 15, 2008, now Pat. No. 7,887,839, which is a continuation of application No. PCT/US2007/006528, filed on Mar. 14, 2007.

(51) Int. Cl.
  *A61K 9/66*    (2006.01)

(52) U.S. Cl.
  USPC ............ 424/455; 424/451; 548/537; 514/423

(58) Field of Classification Search
  None
  See application file for complete search history.

(56) References Cited

U.S. PATENT DOCUMENTS 7,887,839 B2 * 2/2011 Wen et al. ............. 424/455
8,178,125 B2 * 5/2012 Wen et al. ............. 424/455

* cited by examiner

*Primary Examiner* — Hasan Ahmed
(74) *Attorney, Agent, or Firm* — D. Benjamin Borson; Borson Law Group, PC

(57) ABSTRACT

Oral formulations of G-2MePE including microemulsions, coarse emulsions, liquid crystals, tablets and encapsulated forms of G-2MePE have improved bioavailability than conventional aqueous formulations. In particular, microparticles, nanoparticles and microemulsions can exhibit great neuroprotective effects after oral administration. In a microemulsion formulation, G-2MePE can nearly completely inhibit cerebral infarction in an animal model of stroke even after the stroke had been initiated. Thus, improved oral formulations can be desirably used to treat a variety of neurodegenerative conditions with improved convenience and improved efficacy.

28 Claims, 14 Drawing Sheets

US 8,496,963 B2

ORAL FORMULATIONS OF GLYCYL-2-METHYLPROLYL-GLUTAMATE

PRIORITY CLAIM

This application is a Continuation of U.S. application Ser. No. 13/026,787, filed Feb. 11, 2011 (Now U.S. Pat. No. 8,178,125, issued May 15, 2012), which is a Continuation of U.S. application Ser. No. 12/283,684 filed Sep. 15, 2008 (Now U.S. Pat. No. 7,887,839, issued Feb. 15, 2011), which is a Continuation under 35 U.S.C. 111 of PCT International Patent Application No. PCT/US2007/006528, filed Mar. 14, 2007, which claims priority under 35 U.S.C. §119(e) to U.S. Provisional Patent Application Ser. No. 60/782,148 filed Mar. 14, 2006, titled "Formulations of Glycyl-2-Methylprolyl-Glutamate," Jingyuan Wen, et al, inventors. Each of the aforementioned patents and applications is incorporated expressly herein fully by reference.

FIELD OF INVENTION

This invention relates to orally available formulations of Glycyl-2-Methylprolyl-Glutamate (G-2MePE). In particular, this invention relates to microemulsions, liquid crystals and encapsulated formulations of the neuroprotectant, G-2MePE, to methods of making them, to pharmaceutical compositions containing them, and to their use in treating neurological disorders.

BACKGROUND

U.S. Pat. No. 7,041,314, entitled "GPE Analogs and Peptidomimetics," filed May 24, 2002, claims priority under 35 U.S.C. 119(e) to U.S. Provisional Application No. 60/293,853, filed May 24, 2001, disclosed the composition of matter of G-2MePE and other synthetic GPE analogs and uses of aqueous preparations to protect neurons in vitro to toxic nerve damage. U.S. Pat. No. 7,863,304, issued Jan. 4, 2011, discloses additional synthetic analogs of Glycyl-Prolyl-Glutamate.

U.S. application Ser. No. 11/314,424, entitled "Effects of G-2MePE on neurodegeneration" filed 20 Dec. 2005 (now U.S. Pat. No. 7,605,177, issued Oct. 20, 2009), U.S. application Ser. No. 11/315,784, entitled "Cognitive Enhancement and Cognitive Therapy Using G-2MePE," filed Dec. 21, 2005, now abandoned, and U.S. application Ser. No. 12/903,844, filed Oct. 13, 2010, disclosed methods of use of aqueous preparations of G-2MePE to protect animals against neural damage induced by stroke and traumatic brain injury.

U.S. application Ser. No. 11/398,032, entitled "Treatment of Non-Convulsive Seizures in Brain Injury Using G-2-Methyl-Prolyl Glutamate," filed Apr. 4, 2006 (now U.S. Pat. No. 7,714,020, issued May 11, 2010), disclosed methods for using aqueous formulations of G-2MePE for treating non-convulsive seizures in brains of animals subject to penetrating ballistic brain injury.

However, there is a need in the art to provide improved, orally active formulations that have improved bioavailability and increased efficacy than current aqueous solutions of the G-2MePE.

SUMMARY OF INVENTION

In one aspect this invention provides methods of making oral formulations of G-2MePE as tablets, capsules, emulsions and liquid crystals having improved bioavailability and oral efficacy. Some formulations include microparticles, nanoparticles and/or permeation enhancers. Other aspects this invention provide methods of using oral formulations of G-2MePE to treat neurodegenerative conditions. Microemulsion and microparticle formulations of G-2MePE can provide substantially improved neuroprotective effects than aqueous solutions, and can impart desired pharmacokinetic properties to preparations of G-2MePE, thereby improving therapeutic efficacy and duration.

BRIEF DESCRIPTION OF THE FIGURES

This invention is described with reference to specific embodiments thereof. Other features of embodiments of this invention can be appreciated from the Figures, in which.

DETAILED DESCRIPTION

Definitions

Figure 1:
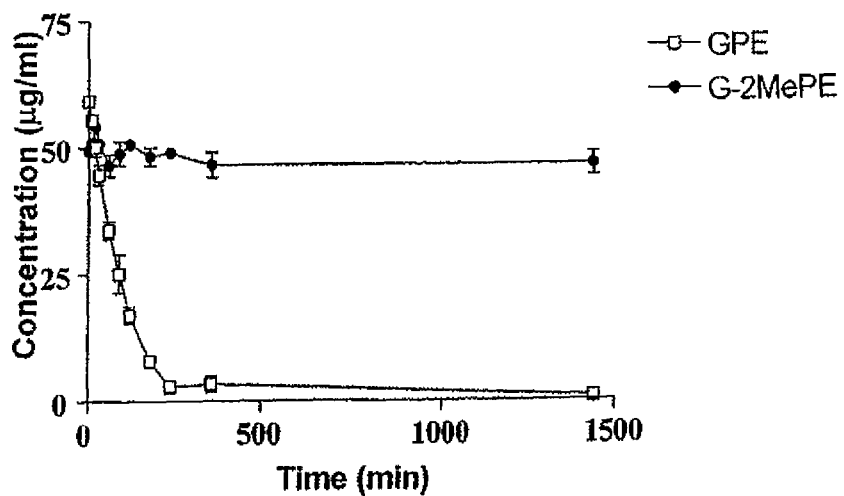
FIG. 1 depicts a graph stability of GPE and G-2MePE (G-2MePE) in presence of a Caco-2 cell monolayer.

The term "about" with reference to a dosage or time refers to a particular variable and a range around that variable that is within normal measurement error or is within about 20% of the value of the variable.

The term "animal" includes humans and non-human animals, such as domestic animals (cats, dogs, and the like) and farm animals (cattle, horses, sheep, goats, swine, and the like).

The term "disease" includes any unhealthy condition of an animal including particularly Parkinson's disease, Huntington's disease, Alzheimer's disease, multiple sclerosis, diabetes, motor disorders, seizures, and cognitive dysfunctions due to aging.

The term "injury" includes any acute damage of an animal including non-hemorrhagic stroke, traumatic brain injury, perinatal asphyxia associated with fetal distress such as that following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, cerebral trauma and toxic injury.

"Memory disorders" or "cognitive disorders" are disorders characterized by permanent or temporary impairment or loss of ability to learn, memorize or recall information. Memory disorder can result from normal aging, injury to the brain, tumors, neurodegenerative disease, vascular conditions, genetic conditions (Huntington's disease), hydrocephalus, other diseases (Pick's disease, Creutzfeldt-Jakob disease, AIDS, meningitis), toxic substances, nutritional deficiency, biochemical disorders, psychological or psychiatric dysfunctions. The presence of memory disorder in a human can be established thorough examination of patient history, physical examination, laboratory tests, imagining tests and neuropsychological tests. Standard neuropsychological tests include but are not limited to Brief Visual Memory Test-Revised (BVMT-R), Cambridge Neuropsychological Test Automated Battery (CANTAB), Children's Memory Scale (CMS), Contextual Memory Test, Continuous Recognition Memory Test (CMRT), Controlled Oral Word Association Test and Memory Functioning Questionnaire, Denman Neuropsychology Memory Scale, Digit Span and Letter Number. Sequence sub-test of the Wechsler Adult Intelligence Scale-III, Fuld Object Memory Evaluation (FOME), Graham-Kendall Memory for Designs Test, Guild Memory Test, Hopkins Verbal Learning Test, Learning and Memory Battery (LAMB), Memory Assessment Clinic Self-Rating Scale (MAC-S), Memory Assessment Scales (MAS), Randt Memory Test, Recognition memory Test (RMT), Rey Auditory and Verbal Learning Test (RAVLT), Rivermead Behavioural Memory Test, Russell's Version of the Wechsler Memory Scale (RWMS), Spatial Working Memory, Test of Memory and Learning (TOMAL), Vermont Memory Scale (VMS), Wechsler Memory Scale, Wide Range Assessment of Memory and Learning (WRAML).

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The term "pharmaceutically acceptable salt" means a salt that is pharmaceutically acceptable and has the desired pharmacological properties. Such salts include salts that can be formed where acidic protons present in the compounds react with inorganic or organic bases. Suitable inorganic salts include those formed with the alkali metals, e.g. sodium and potassium, magnesium, calcium, and aluminum. Suitable organic salts include those formed with organic bases such as amines e.g. ethanolamine, diethanolamine, triethanolamine, tromethamine, N-methylglucamine, and the like. Salts also include acid addition salts formed by reaction of an amine group or groups present in the compound with an acid. Suitable acids include inorganic acids (e.g. hydrochloric and hydrobromic acids) and organic acids (e.g. acetic acid, citric acid, maleic acid, and alkane- and arene-sulfonic acids such as methanesulfonic acid and benzenesulfonic acid). When there are two acidic groups present in a compound, a pharmaceutically acceptable salt may be a mono-acid mono-salt or a di-salt; and similarly where there are more than two acidic groups present, some or all of such groups can be sialified. The same reasoning can be applied when two or more amine groups are present in a compound.

The term "therapeutically effective amount" means the amount of an agent that, when administered to an animal for treating a disease, is sufficient to effect treatment for that disease as measured using a test system recognized in the art.

The term "treating" or "treatment" of a disease may include preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "functional deficit" means a behavioral deficit associated with neurological damage. Such deficits include deficits of gait, as observed in patients with Parkinson's disease, motor abnormalities as observed in patients with Huntington's disease. Functional deficit also includes abnormal foot placement and memory disorders described herein.

The term "G-2MePE" or "NNZ-2566" means the tripeptide analog Glycyl-2-Methylprolyl Glutamate.

The term "seizure" means an abnormal pattern of neural activity in the brain that results in a motor deficit or lack of motor control resulting in abnormal motion, including spasmodic motion. "Seizure" includes electroencephalographic abnormalities, whether or not accompanied by abnormal motor activity.

Treatment of Neurological Disorders

Neurological disorders involving degeneration or death of neurons have been considered to be very difficult to treat. Until recently, no methods were available to reverse degeneration of nerve cells or to successfully treat neurogeneneration. Such conditions include chronic conditions such as Alzheimer's disease, Parkinson's disease, Huntington's disease and other well-known chronic conditions. Additionally, acute conditions involving neurodegeneration include traumatic brain injury or "TBI" (including penetrating ballistic brain injury or "PBBI", and blunt force trauma), stroke, myocardial infarction (MI) cardiac arterial bypass graft surgery (CABG), hypoxia/ischemia (HI) and other well-known conditions.

Recently, several new approaches to treating neurodegeneration have appeared. These include the use of insulin-like growth factor-1 (IGF-1), the N-terminal tripeptide of IGF-1, namely, glycyl-prolyl-glutamate (GPE), analogs of GPE, and synthetic analogs of GPE. One of those, namely glycyl-2-methylprolyl-glutamate (G-2MePE) has been described in U.S. Pat. No. 7,041,314, titled "GPE Analogs and Peptidomimetics," issued May 9, 2006 and herein expressly incorporated fully by reference describes the synthesis and use of synthetic analogs of GPE.

Additionally, U.S. patent application Ser. No. 11/315,784; publication No: U.S. 2007/0004641 titled "Cognitive Enhancement and Cognitive Therapy Using Glycyl-L-2-Methylprolyl-L-Glutamate," filed Dec. 21, 2005 describes effects of G-2MePE to improve cognition in rats in vivo.

U.S. application Ser. No. 11/314,424 titled "Effects of Glycyl-2-Methylprolyl Glutamate on Neurodenegration," describe effects of G-2MePE on traumatic brain injury, a stroke model in rats induced by endothelin-1, in vitro neuroprotection caused by toxins, hypoxic ischemic injury in vivo, in the in vivo model of multiple sclerosis, experimental autoimmune encephalopathy (EAE).

U.S. patent application Ser. No. 11/398,032 filed Apr. 4, 2006 titled "Treatment of Non-Convulsive Seizures in Brain Injury Using G-2-Methylprolyl Glutamate," describes use of 0-2MePE to treat seizures that are "silent" that is, do not have an overt motor component. Such non-convulsive seizures can be associated with traumatic brain injury, stroke, hypoxia/ischemia and toxic injury.

Although the above patent applications demonstrate manufacture and utility of 0-2MePE, it is desirable to produce formulations that have improved pharmacokinetic (PK) or pharmacodynamic (PD) properties. The formulations of this invention meet those needs.

In addition to G-2MePE as described herein, a composition may optionally contain, in addition to a compound of this invention, at least one additional neuroprotective agent selected from, for example, growth factors and associated derivatives (insulin-like growth factor-I (IGF-I), insulin-like growth factor-II (IGF-II), transforming growth factor-$\beta$1, activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF-2, FHF-3 and FHF-4, keratinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue [ORG 2766] and dizolcipine (MK-801), selegiline; glutamate antagonists such as, NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin $\alpha$4 receptors ($\alpha$4$\beta$1 and $\alpha$4$\beta$7), such as anti-MAd-CAM-1mAb MECA-367 (ATCC accession no. HB-9478). Most of these agents, especially the peptides such as the growth factors, and the like are not orally active, and can benefit from administration by injection, infusion or incorporation into an orally acting formulation of this invention.

Administration

Formulations of this invention can be administered after or before onset of a condition that is likely to result in neurodegeneration or a symptom thereof. For example, it is known that hypoxia/ischemia can occur during coronary artery bypass graft (CABG) surgery. Thus, a patient can be pretreated with a compound of this invention before being placed on an extracorporeal oxygenation system. In some embodiments, it can be desirable to administer a compound of this invention beginning about 4 hours before surgery or before an event that is likely to lead to traumatic or other neurological injury. In some embodiments, formulations of our invention can be sub-acutely administered to patients recovering from stroke, TBI, CABG, or any other neurological insult resulting in neurodegeneration or a symptom thereof. In other embodiments, such formulations can be administered to patients suffering from cognitive disorders. In yet other embodiments, such formulations can be administered to patients suffering from functional deficits associated with neurological damage.

Oral Administration of G-2MePE

Oral delivery is among the safest, most convenient and economical methods of drug delivery. The therapeutic advantage of today's orally delivered products centres on the superior predictability and control of delivery of active ingredients, which leads to improved therapeutic efficacy and reduced side effects. This, combined with a decreased frequency of administration, improves patient compliance and, therefore, treatment outcomes. Oral drug-delivery is also typically associated with a low risk of infection, as the body's natural defence mechanisms are not breached during administration.

In order to obtain desired therapeutic effects, neuroprotective agents, especially peptides or analogs of peptides, are preferably administered using formulations and delivery systems that maintain drug stability and allow delivery to the optimum target tissue. Unless suitable formulation strategies are used, the bioavailability of orally administered peptides may be low due to the biochemical and physical barriers that limit absorption. Moreover, the blood brain barrier (BBB)

also can present a formidable obstacle in the delivery of drugs to the brain following peripheral administration. The BBB is composed of a specialized network of microvascular endothelial cells and is responsible for the selective transport of molecules from the systemic compartment into the central nervous system (CNS).

There are many factors of a biochemical, physiological and physicochemical nature, as well as formulation dosage forms that determine the extent of a drug's absorption, biodistribution and pharmacological effects after oral administration. For peptides in particular, these factors include: the intestinal permeability, enzymatic stability, type of delivery system and the transit time of the formulation. Among these factors, the biochemical barriers and physical barriers can be important in influencing the efficacy of orally administered peptides. These two barriers have to be overcome using rational delivery systems before targeting peptides across the BBB. The rational design of orally active peptide formulations should be based on one or more of the following strategies: (a) inhibit or modulate proteolytic activity that degrades the peptide, (b) enhance paracellular or transcellular transport of the peptide, (c) improve peptide penetration through the mucous barrier, (d) increase the half-life of the peptide in circulation for those peptides that require a sustained presence for therapeutic efficacy, (e) develop protease-resistant peptide analogues that retain biological activity, and/or (f) stabilize the peptide by conjugation to carrier molecules or by encapsulation.

Bearing that in mind we have designed formulation strategies suitable to G-2MePE, in order to maximise its stability during storage, protect G-2MePE from the proteolytic enzymes of the intestinal tract and release the peptides sites in the gastrointestinal tract favourable for absorption, and to improve the absorption of drug across the intestinal epithelium.

We have unexpectedly found that formulations of G-2MePE into microemulsions, coarse emulsions, liquid crystals, and encapsulation can provide desirable properties, making these formulations useful in treating conditions characterized by neural degeneration or death.

In certain embodiments, this invention provides pharmaceutical preparations comprising a water-in-oil emulsion.

Emulsions Containing G-2MePE

In some embodiments the water-in-oil emulsion contains an oily phase, composed of long chain carboxylic acids or esters or alcohols thereof, a surfactant or a surface active agent, and an aqueous phase containing primarily water and G-2MePE.

Lipids and Alcohols

Long chain carboxylic acids are those ranging from $C_{16}$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated glycerides such as distilled acetylated monoglycerides; mixtures of propylene glycol monoesters, distilled monoglycerides, sodium stearoyl lactylate and silicon dioxide; d-alpha tocopherol polyethylene glycol 1000 succinate; mixtures of mono- and di-glyceride esters such as Atmul; calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$-$C_{30}$ cholesterol/lavosterol esters; and sucrose long chain carboxylic acid esters.

Examples of the self-emulsifying long chain carboxylic acid esters include those from the groups of stearates, pamitates, ricinoleates, oleates, behenates, ricinolenates, myristates, laurates, caprylates, and caproates.

The alcohols useful in the invention are exemplified by the hydroxyl forms of the carboxylic acids exemplified above and also strearyl alcohol.

In some embodiments the oily phase may comprise a combination of 2 or more of the long chain carboxylic acids or esters or alcohols thereof.

In some embodiments the oil phase may comprise a mixture of caprylic/capric triglyceride and C8/C10 mono-/di-glycerides of caprylic acid.

Surface Active Agents

Surface active agents or surfactants are long chain molecules that can accumulate at hydrophilic/hydrophobic (water/oil) interfaces and lower the surface tension at the interface. As a result they can stabilise an emulsion. In some embodiments of this invention, the surfactant may comprise: Tween® (polyoxyethylene sorbate) family of surfactants, Span® (sorbitan long chain carboxylic acid esters) family of surfactants, Pluronic® (ethylene or propylene oxide block copolymers) family of surfactants, Labrasol®, Labrafil® and Labrafac® (each polyglycolyzed glycerides) families of surfactants, sorbitan esters of oleate, stearate, laurate or other long chain carboxylic acids, poloxamers (polyethylene-polypropylene glycol block copolymers or Pluronic®), other sorbitan or sucrose long chain carboxylic acid esters, mono and diglycerides, PEG derivatives of caprylic/capric triglycerides and mixtures thereof or mixture of two or more of the above.

In some embodiments the surfactant phase may comprise a mixture of Polyoxyethylene (20) sorbitan monooleate (Tween 80®) and sorbitan monooleate (Span 80®).

The aqueous phase may comprise G-2MePE suspended in water and a buffer. In some embodiments G-2MePE will be present in the aqueous phase at the concentration of 1 mg to 300 mg/ml.

In some embodiments, such emulsions are coarse emulsions, microemulsions and liquid crystal emulsions. In other embodiments such emulsion may optionally comprise a permeation enhancer. For aqueous agents, such as G-2MePE, it can be especially desirable to incorporate the drug in the water phase of an emulsion. Such "water-in-oil" formulations provide a suitable biophysical environment for the drug and can provide an oil-water interface that can protect the drug from adverse effects of pH or enzymes that can degrade the drug. Additionally, such water-in-oil formulations can provide a lipid layer, which can interact favorably with lipids in cells of the body, and can increase the partition of the formulation onto the membranes of cells. Such partition can increase the absorption of drugs in such formulations into the circulation and therefore can increase the bioavailability of the drug.

In other embodiments, microparticles or nanoparticles containing encapsulated microemulsion, coarse emulsion or liquid crystal can advantageously be used. In still other embodiments, tablets containing G-2MePE and binders, excipients and optionally with an enteric coating can be advantageously used. These formulations can protect the G-2MePE from degradation in the stomach and can aid in transport of the drug to sites in the gastrointestinal tract where absorption can be accomplished.

We have surprisingly found that certain formulations of G-2MePE have unexpected properties compared to other, more well-known neuroprotective agents. Further, we have unexpectedly found that G-2MePE behaves differently from typical aqueous solutes, including aqueous solutions of G-2MePE.

EXAMPLES

The following examples are intended to illustrate embodiments of this invention, and are not intended to limit the scope to these specific examples. Persons of ordinary skill in the art can readily appreciate that the teachings and disclosures of the present application provide guidance for developing other, obvious variations. All of those variations are considered to be part of this invention.

Example 1

Caco-2 Cell Line from Human Colon Carcinoma

An in vitro model was established to screen compounds for suitability for oral delivery. The initial aim was to overcome the enzymatic and physical barriers to improve neuroprotective peptides absorption across the GI tract.

The Caco-2 cell line has been widely used to mimic the behaviour of the intestine (see U.S. Pat. No. 5,824,638). The Caco-2 line was successfully established and was maintained routinely in the tissue culture lab. During the last two decades the Caco-2 cell culture system has been accepted as a suitable in vitro model for the rapid screening of the intestinal drug absorption. Caco-2 cells, originally isolated from a human colon adenocarcinoma, were routinely cultured as confluent cells in a Transwell cell-culture plate. Upon differentiation in culture, they exhibit correct morphology and exhibit many of the brush border hydrolase enzymes, ion transport properties and carrier systems typical of human gut epithelium. In addition, mature intact Caco-2 cell cultures exhibit a characteristic transepithelial electrical resistance (TEER), which reflects the presence of tight junction complexes between neighbouring cells and inherent ion transport functions of intestinal cells. Similar to normal human intestinal mucosa, Caco-2 cells have remarkable amounts of Phase I (i.e. cytochrome P450 1A1 and 1A2) and Phase II (i.e. UDG-glucuronosyl-transferases) drug metabolising enzymes, as well as drug transporters such as P-protein, and the like. Therefore, the Caco-2 cell culture system has been extensively used to study the transport of small molecular weight drugs (hydrophilic and lipophilic) and therapeutic peptides, and the mechanisms involved. Therefore, results obtained using Caco-2 cell cultures are predictive of absorption of drugs by the intestines of human beings.

Example 2

Stability of GPE and G-2MePE in the Presence of Caco-2 Cells

Purpose

The purpose of this study was to investigate the enzymatic stability of GPE and G-2MePE in the presence of the peptidases present in Caco-2 cell cultures.

Methods

Caco-2 colon carcinoma cells were obtained from American Type Culture Collection (ATCC) and maintained in culture in high glucose DMEM with 10% foetal calf serum, plus penicillin/streptomycin (Pen/Strep) at 37° C., in 5% $CO_2$. Cells were subcultured for approximately 5-7 days. 50-100 μg/ml GPE and 50-100 μg/ml G-2MePE respectively were incubated with Caco-2 monolayer in hanks balanced Salt Solution (HBSS) buffer (pH 7.4) in T75 flask at 37° C. and exposed to 5% $CO_2$ in air. Samples were collected at 0, 15, 30, 45, 60, 120, 150, 180, 210, 240, 360 and 1440 min.

The collected samples were extracted by adding 400 μl of 0.04M sulphuric acid into test tubes, each of which contained 50 μl of a sample. The test tubes were left on ice for 5 min and vortexed. The 50 μl of 10% sodium tungstate was added to each tube and the tubes were vortexed immediately and left on ice for 10 min, vortexed again and left on ice for another 10 min. The cells were centrifuged at 20,000 g at 4° C. for 20 min. The supernatant was collected for testing.

Intact GPE and G-2MePE and their metabolites were analysed by high pressure liquid chromatography (HPLC) on an Aqua 5μ, 250×4.6 mm, C18 column (Phenomenex, Auckland, New Zealand) connected to a Waters 2695 Alliance separation model and a Waters 2996 PDA detector at an absorbance set at 200 nm. The protein content of samples was measured by Lowry assay.

Results

Four metabolites from the degradation of GPE were identified in the presence of Caco-2 cells. G-2MePE was more resistant to enzymatic degradation by enzymes of Caco-2 cells than GPE (FIG. 1). No metabolites were found for the G-2MePE analogue, confirming its stability in the presence of Caco-2 cells.

Conclusion

We conclude that G-2MePE is enzymatically stable in contact with intestinal epithelial cells.

Example 3

Enzymatic Stability of G-2MePE in the Presence of Caco-2 Cells at Different pH

Purpose

The purpose of these studies was to determine the effect of pH on the degradation of G-2MePE by Caco-2 cells.

Methods

100 μg/ml G-2MePE was added to the apical side of confluent cultures of Caco-2 cells in different pH conditions. Samples were taken at 0, 15, 30, 45, 60, 90, 120, 150, 180, 210, 240 min later. Samples were centrifuged at 20,000 g for 15 min and 50 μl supernatant was injected to the column of HPLC. G-2MePE and metabolites were analysed on an Aqua 5u 250×4.6 mm C18 column (Phenomenex, Auckland, New Zealand) connected to a Waters 2695 Alliance separation model and a Waters 2996 PDA detector at an absorbance set at 210 nm. Peptidolytic activity and half-life of G-2MePE were then determined in different pH condition.

Results

Figure 2:
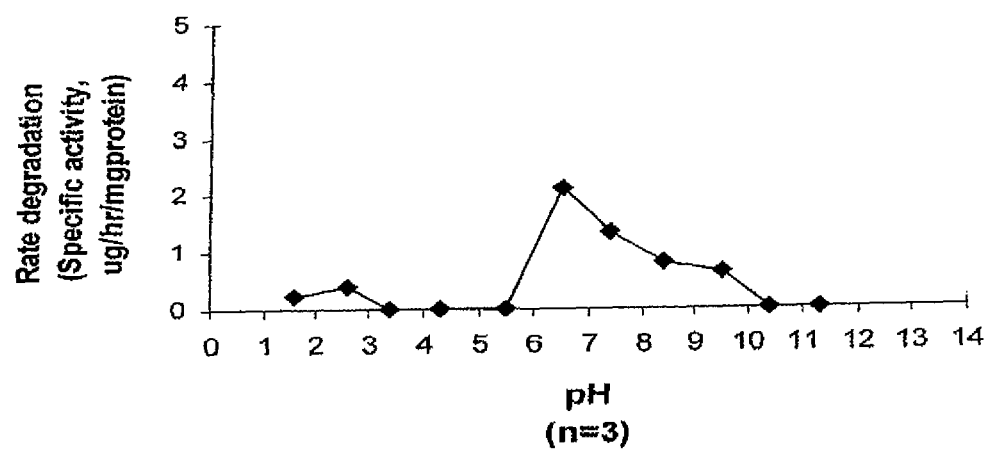
FIG. 2 depicts a graph of the effect of pH on the stability of G-2MePE in the presence of Caco-2 cells.

The highest peptidolytic activity of G-2MePE was observed at a pH of 6.5. The lowest peptidolytic activity of G-2MePE was observed under acidic conditions having a pH of less than 5.5 (FIG. 2). Moderate degradation of G-2MePE was also found in basic conditions (pH 7-9.5).

Conclusion

G-2MePE is stable at pH≦5.5. Thus, G-2MePE is likely to be protected in the relatively acidic environment of the stomach (e.g., pH<3.0), but is likely to be less protected in more neutral environment of the duodenum, ileum or colon.

Example 4

Enzymatic Degradation of GPE in the Presence of Inhibitors

Purpose

The purpose of this study was to determine whether Caco-2 cell peptidases or proteases can degrade GPE. The rationale was that if GPE can be enzymatically degraded by Caco-2 cells, then G-2MePE might also be subject to enzymatic degradation. Inhibition of such degradation can improve bioavailability of G-2MePE.

Methods

GPE was incubated with confluent cultures of Caco-2 cells in the absence or presence of the enzyme inhibitors SDA (bile salt) and EDTA for 4 h. Samples were collected at different time points. Intact GPE was analysed by HPLC and the protein content of samples was estimated by Lowry assay. Percentage of inhibition was used to evaluate the effectiveness of bile salts and EDTA at inhibiting degradation of GPE.

Results

Figure 3:
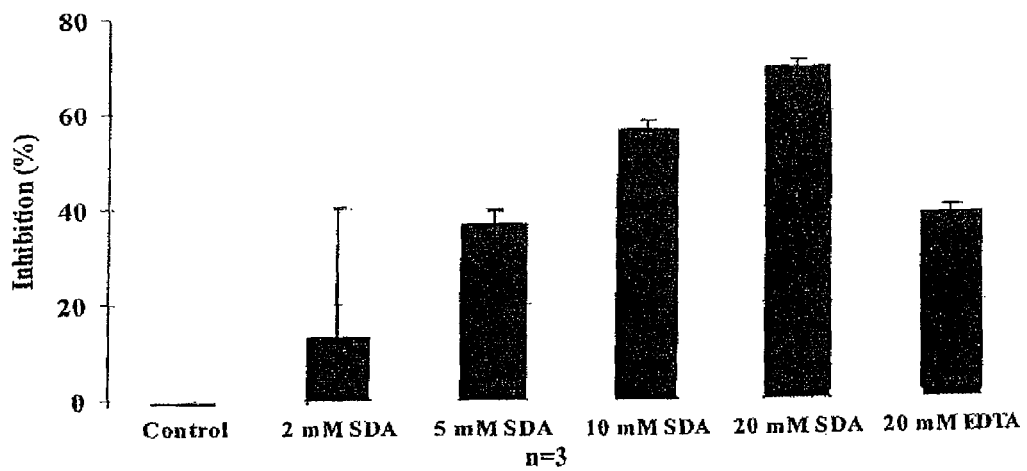
FIG. 3 depicts a graph of the effect of enzyme inhibitors, on the degradation of GPE by Caco-2 cells.

The effects of bile salt (SDA) and EDTA on peptidolysis of GPE in the presence of cultured Caco-2 cells are shown in FIG. 3. Degradation of GPE was significantly inhibited by SDA (≧5 mM) and EDTA (≧20 mM). The rank order of the effectiveness for the preventing GPE peptidolysis in the presence of Caco-2 was SDA (20 mM)>SDA (10 mM)>EDTA (20 mM)>SDA (5 mM)>SDA (2 mM). The inhibition of peptidolysis of GPE was proportional to the dose of SDA used.

Conclusion

This In vitro study demonstrated that peptidases including aminopeptidases and endopeptidases can be involved in the degradation of GPE by Caco-2 cells. SDA (5-20 mM) and EDTA (20 mM) showed significant inhibition in preventing such degradation (FIG. 3). Thus, inclusion of peptidase or protease inhibitors can improve bioavailability of G-2MePE.

Example 5

Cytotoxicity of GPE and G-2MePE

Purpose

The purpose of this study growth was to determine if GPE and/or G-2MePE can inhibit growth of cells. The rationale is that if G-2MePE inhibits intestinal cell growth, such inhibition of growth could limit the doses of G-2MePE that may be tolerated. We used sulforhodamine B (SRB) and determined the 50% inhibitory concentration ($IC_{50}$) necessary to inhibit growth of Caco-2 cells. We wished to determine the safe dose for transport studies across Caco-2 monolayer.

Methods

Sulforhodamine B (SRB) has been shown to be a useful protein stain for use in the quantification of cellular proteins of cultured cells. The dye is believed to bind to basic amino acids of cellular proteins. Thus, colorimetric measurement of the bound dye can provide an estimate cell number. The assay method is simple and reproducible, and the end-point measurements are not time-critical, a significant advantage over assays using tetrazolium derivatives.

Caco-2 cells were purchased from American Type Culture Collection (ATCC) and cells were cultured in sterilized Dulbecco's modified Eagle medium (DMEM), containing 10% foetal calf serum, 1% penicillin-streptomycin-glutamine, 1% nonessential amino acids, and trypsin-EDTA. Sterile T75 flasks, 24-well culture plate, 96-well microtiter plate, centrifuge tubes and tips were purchased from Life Technologies Inc. (Auckland, New Zealand). Sulforhodamine B (SRB), trichloroacetic acid (TCA), acetic acid, unbuffered Tris base (pH 10.5) and D-glucose were purchased from Sigma-Aldrich Chemicals Co. (Auckland, New Zealand). Trypan blue and N-[2-hydroxyethyl]piperazine-N'-[4-butanesulfonic acid] (HEPES) were from Gibco. 12-well Transwell insets (permeable polycarbonate membrane, 24 and 12 mm diameter, 0.4 μm pore size) and plates were purchased from Corning Costar Corp. (NY, USA).

GPE and G-2MePE were incubated with Caco-2 cells in 96-well plates for 24, 48, 72, 96 or 120 h. The cells were fixed by TCA and SRB was added to each well. Cell-bound dye was extracted with Tris base buffer to solubilize the dye and the absorbance determined by a plate reader at 570 nm. Inhibition of growth was expressed as relative viability (% control) and the $IC_{50}$ was calculated from the concentration-response curves after log/probit transformation.

Results

We found that the $IC_{50}$ of G-2MePE (24-120 hrs.) on Caco-2 cell growth was 1 to 4.6 mM. GPE, even at concentration of 15 mM, inhibited the growth of Caco-2 cells by only 35%; therefore, $IC_{50}$ of Caco-2 cell growth by GPE was ≧15 mM (Table 1).

TABLE 1

| ($IC_{50}$) of Growth of Caco-2 Cells in the Presence of G-2MePE | |
|---|---|
| Time (hours) | $IC_{50}$ of G-2MePE (mM) |
| 24 | 4.64 |
| 48 | 3.66 |
| 72 | 2.24 |
| 96 | 1.09 |
| 120 | 1.01 |

In U.S. Pat. No. 7,041,314, we found that G-2MePE was an effective neuroprotective compound in vitro at concentrations ranging from 10 nm to 1 mM, with a broad plateau of effective concentrations from 10 nM to 10 μM (see FIG. 15 of U.S. Pat. No. 7,041,314).

Conclusions

The $IC_{50}$ for G-2MePE is higher than concentrations of G-2MePE known to be neuroprotective in vitro. Thus, we conclude that use of G-2MePE in vivo at concentrations equivalent to those found effective in vitro would not be toxic to intestinal epithelial cells.

Example 6

Permeability of Fluorescein Across Caco-2 Cells

Purpose

The purpose of this study was to determine the appearance permeation coefficient (Papp) and transepithelial electrical resistance (TEER) across confluent cultures of Caco-2 epithelial cells caused by a typical hydrophilic material.

Methods

Integrity of Caco-2 cell cultures was assessed by measuring the TEER and the leakage of $^{14}$C-mannitol or fluorescein across confluent cultures. Inserts with confluent cell cultures and an electrical resistance of greater than 300 $\Omega/cm^2$, were considered appropriate for these studies. Fluorescein or 0.5 $\mu$Ci/50 $\mu$l of $^{14}$C-mannitol was added to the apical cell and incubated for 1-4 hours. The acceptable leakage was considered to be <0.5-1%. 6 inserts with good integrity were chosen and then washed with transport buffer. The medium from all apical and basolateral wells was removed. The cell cultures were washed twice with warm 37° C. transport buffer.

Figure 4:
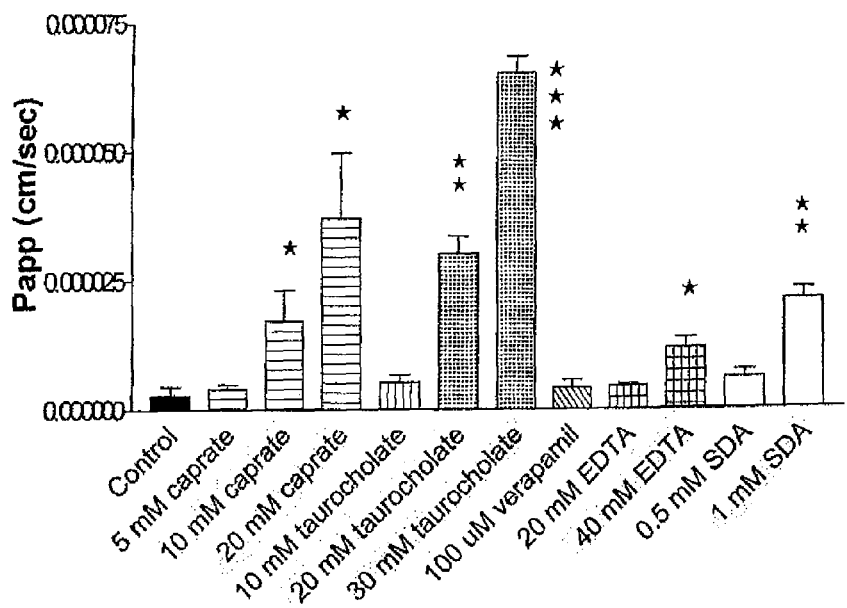
FIG. 4 depicts a graph of effects of permeation enhancers on the transport of sodium fluorescein across Caco-2 cell cultures.

To determine effects of permeation enhancers, sodium fluorescein (MW=376) was incubated in the donor side (above the membrane) of transwells containing Caco-2 cells in the absence or presence of various permeation enhancers, Samples (0.4 ml) were taken from the receptor side (side under the membrane) at 15, 30, 45, 60, 90, 120, 150, 180, 210, 240 and 360 min respectively. The solution on the transwell receptor side was then replaced with 0.4 ml of fresh HBSS, and we collected 0.1 ml from the donor side (then replaced with 0.1 ml sodium fluorescein at the same concentration). The reaction was terminated from donor side by adding the same volume HCl (0.2M) or by 3:1 Acetonitril/methonal with 2% acetic acid to each sample. The samples were centrifuged at 3000 g for 15 min. Supernatants were collected, dried by Speed Vacuum, diluted with mobile phase and the resulting sample was analysed by spectrofluorophotometer. The apparent permeability coefficient was used to compare the permeability between control and treatment groups (FIG. 4). Transepithelial electric resistance (TEER) was measured using a Millipore voltage meter at different time points. The means of TEER values from 30-180 min were compared between the control and treatment group (FIG. 5).

Results

Figure 5:
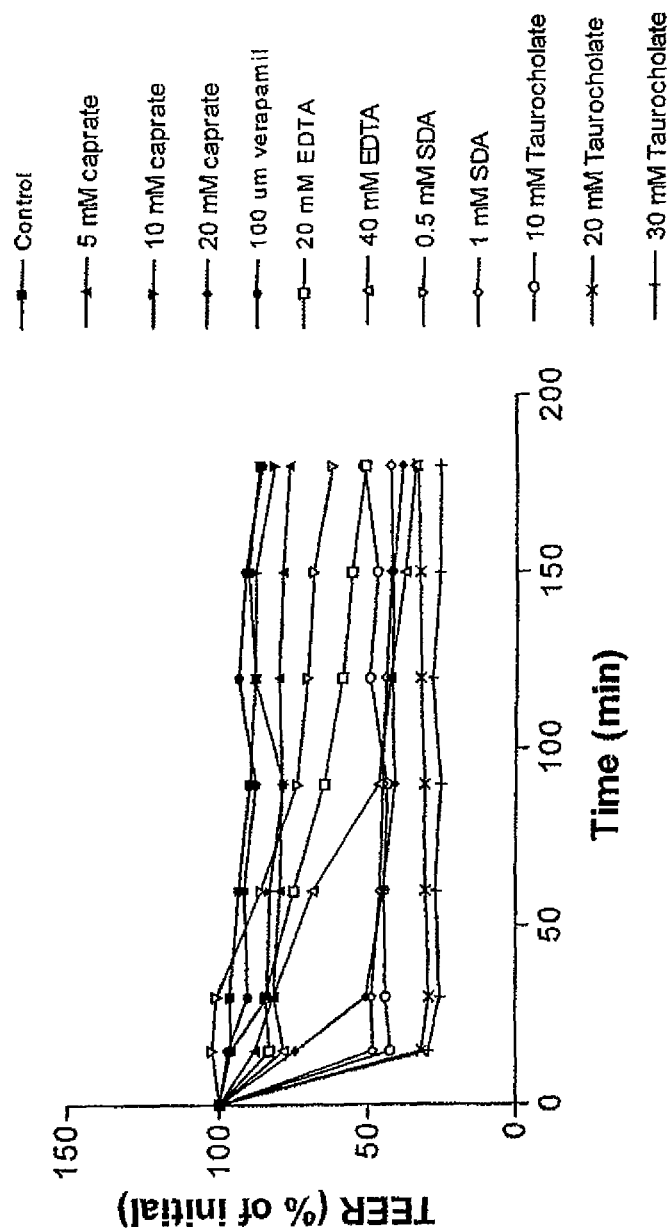
FIG. 5 depicts a graph of effects of permeation enhancers on transepithelial electric resistance (TEER) of Caco-2 cell cultures.

Sodium caprate (10 or 20 mM), taurocholate (30 mM), EDTA (40 mM) and SDA (1 mM), each significantly ($P<0.05$) increased the permeability of the Caco-2 epithelial cell layer to fluorescein and reduced the TEER during the 3 h transport experiment (FIGS. 4 and 5). However, the effect of sodium caprate (20 mM) was greater than the effect of the same concentration of taurocholate (FIG. 4).

Conclusion

Sodium taurocholate ($\geqq$20 mM), caprate ($\geqq$10 mM), EDTA (40 mM) or SDA (1 mM) could be used to improve the permeability of a hydrophilic compound (fluorescein) across Caco-2 epithelial cell layers by affecting transcellular and paracellular pathways.

Example 7

Uptake of G-2MePE by Caco-2 Cells

Purpose

The purpose of this study was to evaluate the uptake of G-2MePE by Caco-2 cells to explore active transport of peptides across intestinal cells and to determine effects of pH of incubation medium, time, temperature and substrate concentration on the uptake of G-2MePE by Caco-2 cells.

Methods

Caco-2 cultures ($5 \times 10^5$ cells in 5 ml DMEM medium) were grown in 60 mm plastic culture dishes. Fresh medium was replaced every 2-3 days. Cells were cultured at 37° C. for 12-14 days for uptake assay study. The uptake assay study was commenced after cells reached confluency, i.e., after 12-14 days in culture. Each dish was washed with HEPES (pH 7.4). G-2MePE was added to each 60 mm culture dish and was incubated at 37° C. Samples were taken at 5 s, 15 s, 30 s, 45 s, 1 min, 2 min, 5 min, 10 min, 15 min, and 30 min and 120 min after adding G-2MePE. The cells were scraped off with a cell scraper into an extraction solution and centrifuged at 20,000 g for 20 min. The supernatant was analysed by HPLC to identify G-2MePE and its metabolites. The pellet was diluted by NaOH to determine the protein content by Lowry assay.

Results and Discussion

Figure 6:
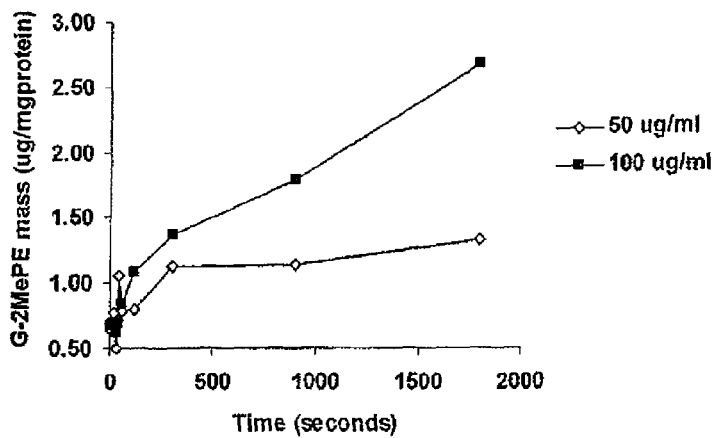
FIG. 6 depicts a graph of uptake of G-2MePE by Caco-2 cells.

This study demonstrated that G-2MePE was taken up by Caco-2 cells (i.e., 1.3%; FIG. 6). The uptake of G-2MePE was time- and dose-dependent.

Example 8

Permeability of G-2MePE Across Caco-2 Cells: Effects of Permeation Enhancers Purpose The purpose of this study was to determine if permeability enhancers can increase transport of G-2MePE across Caco-2 cell layers.

Methods

The integrity of cell cultures was confirmed as described in Example 6. G-2MePE was added in three or six replicates to the donor sides of Transwells containing Caco-2 cells in the absence or presence of various permeation enhancers (FIG. 4), 1.5 ml transport buffer was added to the receptor side. The Transwells were then left to incubate. Samples (0.4 ml each) were taken from the receptor side at different points (15, 30, 45, 60, 90, 120, 150, 180, 210, 240 and 360 min). After each sample was taken, 0.4 ml of fresh HBSS buffer was added to the side of the Transwell from which sample was taken. Subsequently, 0.1 ml donor solution was collected to measure the concentration of the intact G-2MePE. Following each sampling, 0.1 ml of G-2MePE at the same concentration was replaced.

Figure 7:
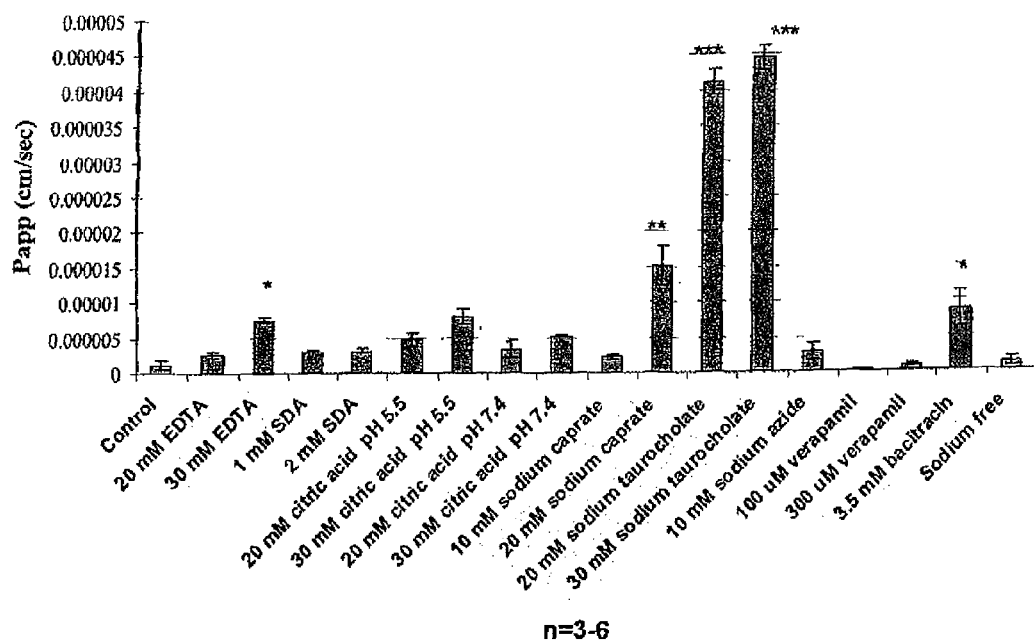
FIG. 7 depicts a graph of effects of permeation enhancers on the transport of 0-2MePE across Caco-2 cell cultures.

Peptidolysis was terminated by adding the same volume of HCl (0.2M) to each sample. The resulting samples were centrifuged at 3000 g for 15 min. Supernatants were collected, dried by Speed Vacuum, diluted with mobile phase and analysed by spectrofluorophotometer. The apparent permeability coefficient was calculated and used to compare the permeability between the control and treatment group (FIG. 7). Transepthelial electric resistance (TEER) was measured using a Millipore voltage meter at different time points. The means of TEER values from 30-180 min were compared between the control group and treatment group.

Results

EDTA (30 mM), sodium caprate (20 mM), taurocholate (20 and 30 mM), citric acid (30 mM) and bacitracin (3.5 mM), significantly increased the permeability of the Caco-2 the epithelial membrane to G-2MePE (FIG. 7). The TEER was significantly reduced by using EDTA (30 mM) or sodium caprate (20 mM), taurocholate (20 & 30 mM), or citric acid (30 mM) (data not shown).

Conclusions

Sodium taurocholate (≧20 mM), caprate (≧10 mM), EDTA (40 mM) or SDA (1 mM) can be used to improve the permeability of G-2MePE across the Caco-2 epithelial cultures, presumably by affecting transcellular and paracellular pathways (FIG. 7).

Notably and quite unexpectedly, the effects of caprate and taurocholate on uptake of fluorescein and G-2MePE were quite different. As noted previously for fluorescein (FIG. 4), 20 mM caprate had greater effect than 20 mM taurocholate. Surprisingly, however, 20 mM taurocholate had dramatically greater effect on uptake of C-2MePE than did 20 mM caprate (FIG. 7). Although the mechanism for this observation is not known, it demonstrates an unexpected property of G-2MePE that differentiates it from fluorescein.

Example 9

Protein Binding of GPE and G-2MePE In Vitro

Purpose

The purpose of this study was to whether binding of serum proteins to GPE and G-2MePE might alter bioavailability of the drugs in vivo. The rationale is that if these drugs are bound by plasma proteins, then the bioavailability of the free (unbound) drug might be reduced, thereby decreasing neuroprotective efficacy.

Methods

An ultrafiltration technique was used to measure the fraction of free GPE and G-2MePE in the presence of bovine serum albumin (BSA) (Sigma, USA). Triplicates of each system (10 ml as total volume) were prepared by mixing various volumes of GPE and G-2MePE (1 g/L) with albumin (88 g/L) or MilliQ water together. The bound and unbound fractions of each system were separated from bovine serum albumin by an Ultrafiltration unit (Centrisare®I with a molecular weight cut-off of 10,000 Daltons, Sartorius, Biolab).

System 1 (left three columns shown in FIGS. 8 and 9) was prepared by mixing 5 ml GPE or 5 ml G-2MePE with 5 ml albumin at the ratio of 1:88, respectively.

System 2 (middle three columns shown in FIGS. 8 and 9) was prepared by mixing 5 ml albumin, 2.5 ml of GPE or G-2MePE and 2.5 ml MilliQ water as the ratio of drug versus albumin was 1:176, respectively.

System 3 (right three columns shown in FIGS. 8 and 9) was prepared by mixing 2.5 ml albumin, 5 ml GPE or G-2MePE and 2.5 ml MilliQ water as the ratio of drug versus albumin is 1:44 respectively. A non-specific control was prepared by mixing 2.5 or 5 ml GPE or G-2MePE and 7.5 or 5 ml water respectively as total initial amount of GPE or G-2MePE in the presence of variable systems. All systems were mixed well and left to stand for one and half an hour at 4° C.

A 2 ml sample was taken from each individual system and transferred into a separate ultrafiltration unit. All samples were equilibrated at 25° C. before centrifuging. Triplicate samples were precentrifuged at 1000 g for 5 min to give enough contact time between samples with membranes of the units. After precentrifugation, all samples were centrifuged at 2500 g for 30 min. Unbound GPE or G-2MePE (the filtrate) of each individual system in the ultrafiltrate (Cu) was then carefully removed into dry labelled tubes and were analyzed by HPLC on an Aqua 5u 250×4.6 mm C18 column (Phenomenex, Auckland, New Zealand) connected to a Waters 2695 Alliance separation model and a Waters 2996 PDA detector with an absorbance measured at 210 nm. The percent of GPE or G-2MePE bound was determined from the following equation:

$$\% \text{ bound } GPE \text{ or } G\text{-}2MePE = \left[1 - \frac{Cu}{Ct}\right] \times 100$$

where:

Ct denotes the total GPE or G-2MePE concentration present in Ultrafiltration unit prior to its incubation with albumin;

Cu denotes unbound GPE or G-2MePE concentration present in the Ultrafiltration unit after incubation with albumin.

Results

Figure 8:
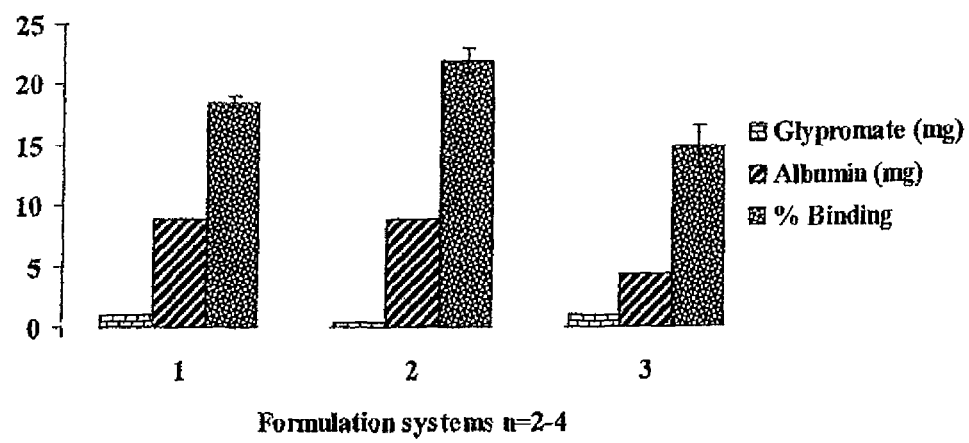
FIG. 8 depicts a graph of protein binding of GPE in vitro by albumin.

The left-hand columns shown for each system in FIG. 8 represent the amounts of GPE (in mg) present in the respective Systems: 1, 2 and 3 prior to incubation with albumin. Middle columns shown for each system, columns in FIG. 8 represent the amount of albumin (in mg) present in systems 1, 2 and 3, prior to the incubation with GPE. Right-hand columns for each system in FIG. 8 represent the percentage of binding of GPE to albumin.

Figure 9:
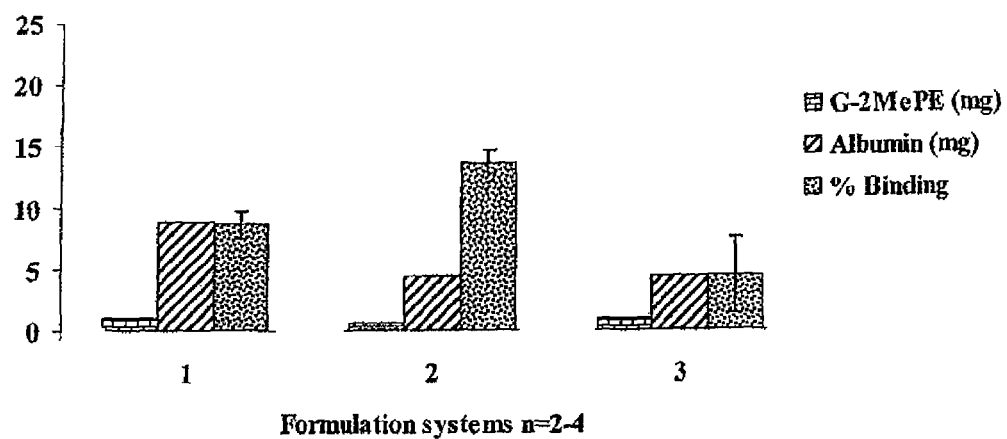
FIG. 9 depicts a graph of protein binding of G-2MePE in vitro by albumin.

The left-hand columns shown for each system in FIG. 9 represent the amounts of G-2MePE (in mg) present in the respective Systems: 1, 2 and 3 prior to incubation with albumin. Middle columns for each system shown in FIG. 9 represent the amounts of albumin (in mg) present in systems 1, 2 and 3, prior to the incubation with G-2MePE. Right-hand columns for each system in FIG. 9 represent the percentage of binding of G-2MePE to albumin.

G-2MePE showed less protein binding than GPE, with the level of binding being proportional to the amount of protein used (FIGS. 8 and 9).

Conclusions

We unexpectedly found that G-2MePE has lower protein binding than GPE, making G-2MePE suitable for in vivo use. As can be discerned by comparing FIGS. 8 and 9, at the highest ratio of drug to protein (1:88 and 1:44), less of the G-2MePE was bound to albumin. In contrast, at the same drug:protein ratio (1:88 and 1:44), more of the GPE remained bound. Although the mechanism for this surprising phenomenon remains unexplained, the degree of drug-plasma protein binding can markedly affect pharmacokinetic and pharmacodynamic properties of a drug. This is due to the fact that having a lower molecular size, unbound drug can more easily penetrate the wall of the blood vessel, whereas the protein bound drug cannot because of its higher molecular size. Furthermore, the drug plasma protein binding is also stereoselective in nature due to the inherent chirality of plasma proteins such as human serum albumin (HSA) and alpha-1-acid-glycoprotein (AGP). Additionally, many therapeutic molecules are not as active while protein bound.

Thus, greater protein binding can decrease the effective concentration of the agent and thereby diminish its therapeutic efficacy. Because G-2MePE can have high bioavailability, G-2MePE can therefore be an effective neuroprotective agent for oral, in vivo use.

Example 10

Enterically Coated Tablets Improve Stability of G-2MePE

Purpose

The purpose of this study was to determine if an enterically coated tablet can provide improved bioavailability of G-2MePE.

Methods

Tablet Preparation

A mixture of 0.14-0.2 g powder containing G-2MePE, citric acid disintegrant, poly-vinyl pyrrolidone, talc, magnesium stearic and lactose was filled into a tablet cavity and directly compressed into tablets. The tablets were coated using a coating solution containing EUDRAGIT® L100-55, dibutyl phthalate, talc and isopropanol. Coating processing was achieved using a specific coating facility. Coating material was about 1% of tablet weight.

BP Disintegration Test

A disintegration test was carried out using 1 l beaker and motorized shaft moving up and down at 30 rpm and carrying a rigid basket containing a rack assembly for the tablets. The assembly consists of individual tubes. Six tablets were introduced into each individual disintegration assembly. Each assembly was suspended in a beaker containing 0.1M hydrochloric acid and operated without the discs for 120 minutes. The assembly was then removed from the liquid and inspected. No tablet showed signs of cracks that would allow the escape of the contents or disintegration, apart from fragments of coating. The 0.1M hydrochloric acid in the beaker was replaced with phosphate buffer pH 7 and a disc was added to each tube. The apparatus was operated for a further 60 minutes at 30 rpm. The tablets passed the test if all six tablets failed to disintegrate.

Results and Conclusion

The enterically coated tablets were formulated and they passed the BP disintegration test. We conclude that enterically coated tablets can be a suitable formulation for oral administration of G-2MePE.

Example 11

G-2MePE Microparticles

Purpose

The purpose of this study was to determine whether microparticles can protect G-2MePE from degradation by enzymes such as pepsin in the stomach. To do this, we carried out a series of experiments in vitro in solutions having different pH.

Methods

Various amounts of G-2MePE or sodium fluorescein were dissolved in EUDRAGIT® FS30D 30% dispersion and transferred to centrifugation tubes. The tubes containing samples were frozen at −80° C. and then transferred into a freeze dryer to dry samples overnight. After drying, the centrifugation tubes were weighed. 20 mg each of microparticle preparation (polymer and drug ratio approximately 20:1; 10:1; 1:5 and 1:2.5) was added to a solution containing either 200 ml of 0.1M HCl or 0.2M phosphate buffer at a pH of 7. Samples were collected at different time points.

To analyse sodium fluorescein, triplicate samples were added into a 96-well plate. The plate was then read using a 495 nm excitation wavelength of and reading the fluorescence at 520 nm using a fluorescence microplate reader (Wallac 1420, Victor, multiple readers). Triplicate samples of G-2MePE were analyzed by HPLC on an Aqua 5μ 250×4.6 mm C18 column (Phenomenex, Auckland, New Zealand) connected to Waters 2695 Alliance separation model and a Waters 2996 PDA detector with an absorbance set at 210 nm.

Results and Conclusions

Figure 10A:
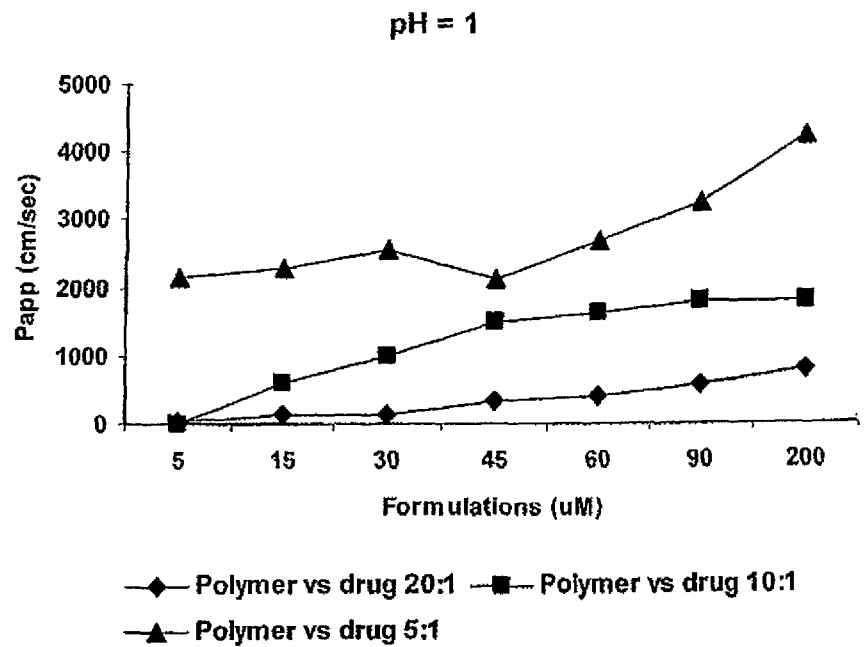
FIG. 10A depicts a graph of the release of sodium fluorescein from microparticles in the medium at pH 1.
Figure 10B:
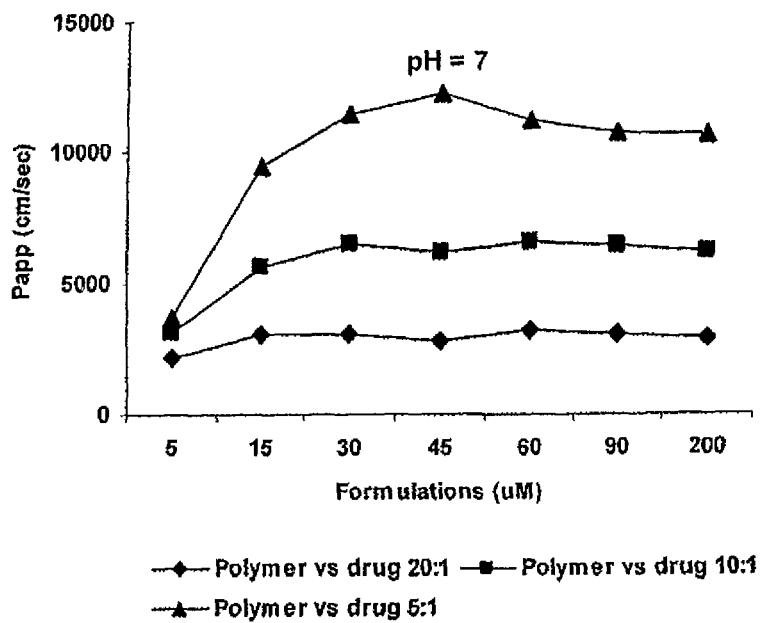
FIG. 10B depicts a graph of the release of sodium fluorsecein from microparticles in the medium at pH 7.
Figure 11:
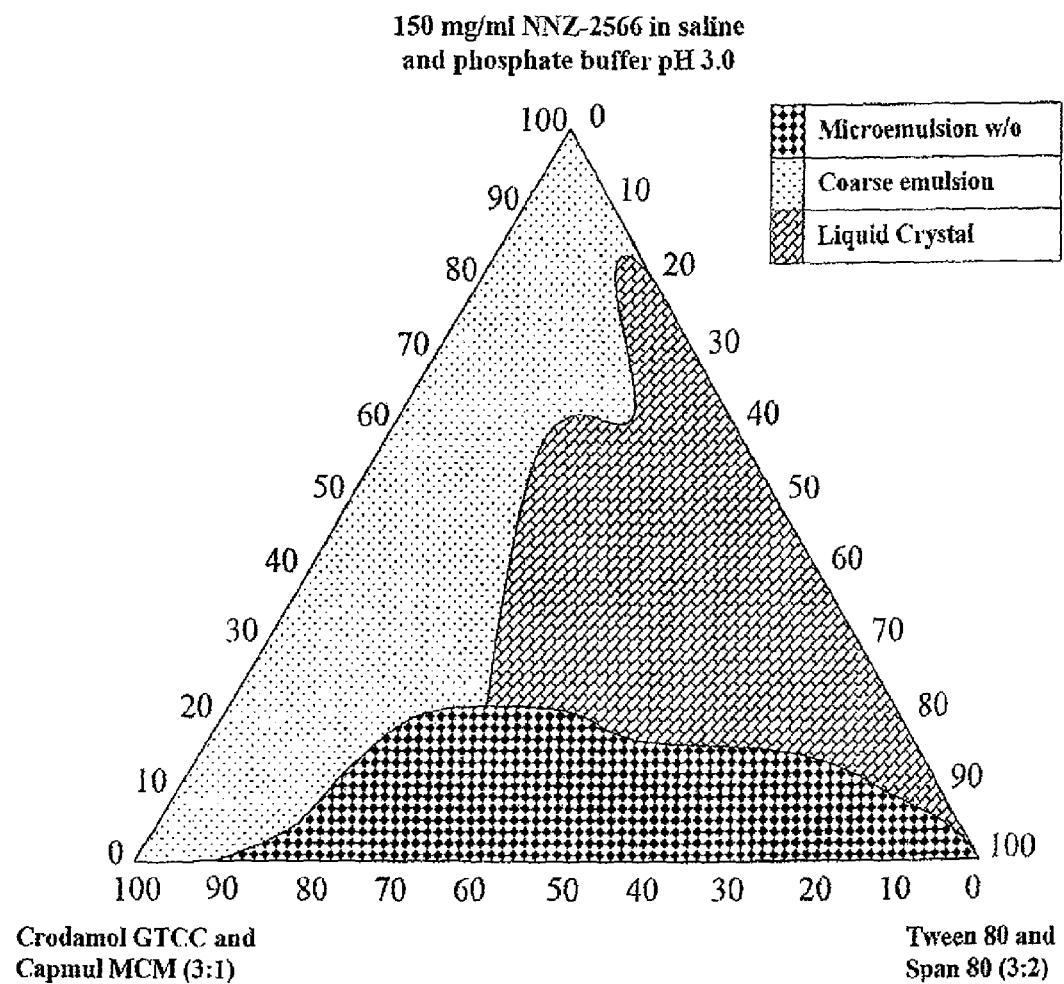
FIG. 11 depicts a graph of a pseudo-tertiary diagram of microemulsions containing G-2MePE.
Figure 12A:
FIG. 12A depicts a photomicrograph of a freeze-fracture transmission electron micrograph of nanocapsules of this invention.
Figure 12B:
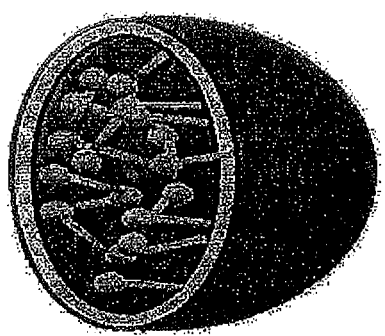
FIG. 12B depicts a schematic diagram showing drug entrapped in a nanocapsule.

Microparticles were prepared and tested in acidic and basic media in vitro. The microparticles that included the enteric coat polymer EUDRAGIT® were resistant to stomach acid and released throughout the intestinal tract. The release from microparticles of sodium fluorescein, a hydrophilic compound model, in pH 7 was approximately 4 times faster than that in pH 1 medium. This result confirmed that the enteric coat polymer can increase the therapeutic efficiency of G-2MePE after oral administration. The microparticles also controlled the time at which substances were released allowing for sustained release (FIGS. 10A and 10B).

We conclude that an enteric coating can delay release of G-2MePE in the stomach, where the pH is low (e.g., <3.0) and increase the release in the duodenum, jejunum, ileum or colon where the pH is closer to neutral.

Example 12

G-2MePE Microemulsions

Purpose

The purpose of this study was to formulate water-in-oil microemulsions containing G-2MePE.

Materials and Methods

Oils:

Caprylic/capric triglycerides (Crodamol GTCC®) was supplied by Chemcolour Industries (NZ) Ltd (Auckland, NZ). C8/C10 mono-/di-glycerides of caprylic acid (Capmul MCM®) were supplied by Abitec Corporation (Janesville, Wis.).

Surfactants:

Polyoxyethylene (20) sorbitan monooleate (Tween 80®) and sorbitan monooleate (Span 80®) were obtained from Sigma-Aldrich Chemie (Steinheim, Germany).

Drugs and Other Chemicals:

G-2MePE was manufactured according to methods described in U.S. Pat. No. 7,041,314, herein incorporated fully by reference. Potassium dihydrogen, potassium chloride and orthophosphoric acid were purchased from Scharlau Chemic. (Barcelona, Spain).

Construction of Pseudo-Tertiary Phase Diagram:

Crodamol GTCC® and Capmul MCM® were weighed separately, mixed together in the ratio of 3 to 1 respectively (45 g:15 g) and vortexed for complete mixing. The surfactants Tween 80® and Span 80® were weighed separately, mixed by weight to a ratio of 3 to 2 respectively (36 g:24 g) and mixed well. 300 mg/ml of G-2MePE stock solution was prepared by suspending 900 mg G-2MePE in 3 ml saline and further diluting the solution with 3 ml phosphate buffer pH3 (ionic strength equals 0.1 mole/liter) (1:1) to the concentration of G-2MePE (150 mg/ml). The aqueous phase containing G-2MePE was left overnight at room temperature to equilibrate. A large number of samples (more than 250 samples) containing oil (mixture of Crodamol GTCC® and Capmul MCM® at the ratio of 3:1), non-ionic surfactants (mixture of Tween 80® and Span 80® at the ratio of 3:2) and aqueous phase containing G-2MePE at a concentration of 150 mg/ml were prepared and left overnight at room temperature to equilibrate. Normal light and polarising light microscopy was used to identify combinations that gave rise to microemulsion, liquid crystals or coarse emulsions.

Preparation of Microemulsions Containing G-2MePE:

Crodamol GTCC® and Capmul MCM® were mixed at ratios described above. Non-ionic surfactants were mixed at the ration described above. G-2MePE-containing stock was prepared as described above. The mixture of Crodamol/Capmul (7.6 g) was added into a small beaker, followed by the addition of the mixture of Tween 80®/Span 80® (2 g) and mixed two of components thoroughly using a magnet stirring at 1000 rpm for 10 min.

The G-2MePE solution (0.4 g) was added dropwise (10 µl per drop) to the mixture prepared above. The ratio of Crodamol/Capmul:Tween 80®/Span 80®:G-2MePE was 7.6:2:0.4 in a 10 g microemulsion system. Microemulsions containing 6 mg G-2MePE per ml microemulsion were identified visually as isotropic, transparent solutions, being thermodynamically stable. Coarse emulsions were identified by their turbidity and isotropy, and liquid crystals were identified by their characteristic birefringence (i.e., not isotropic) and the appearance of interference patterns in polarized light. Such characteristics of liquid crystals can be related to the orientation of molecules parallel to each other in large clusters, visible under a microscope.

Results and Conclusions

A pseudo-tertiary phase diagram (FIG. 11) for the components was constructed and the boundaries of the different regions were identified. ME: microemulsion, LC: liquid crystal, coarse: coarse emulsion. The dotted area in the triangle represents ratios rendering coarse emulsions. The area marked with a brick pattern represents liquid crystal formulations and the area marked with a checked pattern represents microemulsions.

G-2MePE microemulsions were observed to have a uniform droplet size of less than 200 nm. Lipid-based microemulsions offer advantages for the oral delivery of drugs including peptides by improving the stability of drugs as they protect drugs against enzymatic degradation and enhance the absorption of drugs by surfactant-induced increases in membrane fluidity. We conclude that microemulsions, coarse emulsions and liquid crystal formulations can be used to deliver orally available G-2MePE.

Example 13

G-2MePE in Polymeric Nanocapsules (Nac)

Purpose

The purpose of these studies was to develop nanocapsule delivery systems for G-2MePE to protect the compound from degradation and facilitate its transport through the intestinal epithelium.

Methods

Polymeric nanocapsules (Nac) were prepared using interfacial polymerisation methods. First, a microemulsion was prepared using methods described in Example 12. Then, 10 g of microemulsion 2 (MC2) was prepared as described in Example 14 below. 100 mg, 0.150 mg or 300 mg of ECA (ethyl 2-cyanoacrylate) monomer (Sigma, St, Louis, Mo.) was mixed with 300 mg chloroform in an Eppendorf tube and vortexed. The monomer solution was slowly added dropwise to the MC2 under magnetic agitation at 4° C. at approximately 800 rpm and then left to stand overnight to allow polymerisation to occur.

Resulting products were centrifuged at 51,500 g for 60 minutes at 25° C. (Beckman L-70 centrifuge, 70Ti rotor) to isolate the Nacs. After removal of the supernatant, the precipitate was air-dried then dispersed in ethanol by vortex, followed by ultrasonication to remove excess oil and surfactant. This was then centrifuged at ~1600×g for 15 minutes at 25° C. (Sigma 1-13 microcentrifuge). The washing process was repeated three times with each sample to ensure removal of all residue.

The resulting product was then redispersed in Milli-Q water, frozen overnight at −20° C. (Fisher and Paykel Ltd. NZ, Leonard deep freezer) then freeze-dried for 1 day at −52° C. and a vacuum of $30\times10^{-3}$ mbar using a FreeZone® Bulk Tray Dryer System (Labconco, USA).

Results and Conclusions

G-2MePE microemulsion-containing polymeric nanocapsules were small, spherical capsules and generally ranged in size between 100-200 nm in diameter (FIGS. 12A and 12B). Nanocapsules have been used to improve the oral bioavailability of peptides since they can protect peptides from proteolytic degradation. Furthermore, they may pass across the intestinal mucosa; and hence facilitate the absorption of peptides from the intestinal lumen. Nanoparticles have been shown to translocate across the intestinal mucosa by three different pathways: through the Peyer's patches of the GALT, and via the intercellular and intracellular pathways.

We conclude that G-2MePE-containing nanocapsules can be used for effective oral delivery of G-2MePE.

Example 14

Release of G-2MePE from Microemulsions, Liquid Crystals and Coarse Emulsions Purpose The purpose of these studies was to determine the release characteristics of G-2MePE from different phase systems of this invention.

Methods

Drug release studies were performed using vertical Franz cells (model VTC-200). One formulation was chosen from each of the three different phase systems prepared in accordance with Example 12. Microemulsion 1 (MC1) was composed of 60% of GTCC:MCM (3:1), 30% of surfactants (Tween 80®:Span 80®) (3:2) and 10% of 150 mg/ml G-2mePE in phosphate buffer pH 3. Microemulsion 2 (MC2) was composed of 45% of GTCC:MCM (3:1), 25% of surfactants (Tween 80®:Span 80®) (3:2) and 30% of 150 mg/ml of G-2MePE in phosphate buffer pH 3. Liquid crystals were composed of 15% of GTCC:MCM (3:1), 70% of surfactants (Tween 80®:Span 80®) (3:2) and 15% of 150 mg/ml G-2MePE in phosphate buffer, pH 3. A coarse emulsion was composed of 16% of GTCC:MCM (3:1), 14% of surfactants (Tween 80®:Span 80®) (3:2) and 70% of 150 mg/ml G-2MePE in phosphate buffer pH 3). Triplicate samples of 0.25 g G-2MePE in various volumes of above formulations were transferred into Franz cells for drug release studies.

Cellulose membrane dialysis tubing was soaked in water for 24 hours before the commencement of these experiments. This membrane selectively allows the permeation of G-2MePE and avoids the diffusion of the MC constituents into the donor compartment. Throughout this study, drug release profiles were obtained using vertical Franz cells. A vertical Franz cell is comprised of a donor chamber at the top and a receptor chamber underneath which is separated by the dialysis membrane. Samples were taken periodically from the receptor chamber through sampling port. The wall of the receptor chamber was enclosed by a water jacket connected to a heater to maintain a constant temperature within the cell.

The receptor compartment of each of the Franz cells was filled with phosphate buffer at a pH of 7.4, while the donor compartment contained the selected formulation of G-2MePE. The donor compartment was then sealed with an occlusive film (Parafilm™ 'M', Pechiney Plastic Packaging, Chicago, Ill.). Throughout the experiment, three Franz cells were allocated for each formulation prepared as above, in which the receptor medium was maintained at a temperature of ~37° C. Samples (400 µl) were collected from the receptor compartment at 0, 2, 5, 10, 15, 20, 30, 45, 60, 90, 120, 180, 240, 300, 480, 600, 720 and 1440 minutes and refilled as same volume of fresh buffer into the receptor. The absorbance of each sample was measured using a UV spectrophotometer (Biochrom Libra S32 PC) at wavelength of 210 nm. A standard curve was then used to calculate the concentration of G-2MePE in each sample. The drug release profiles were shown in FIG. 13.

Results

Figure 13:
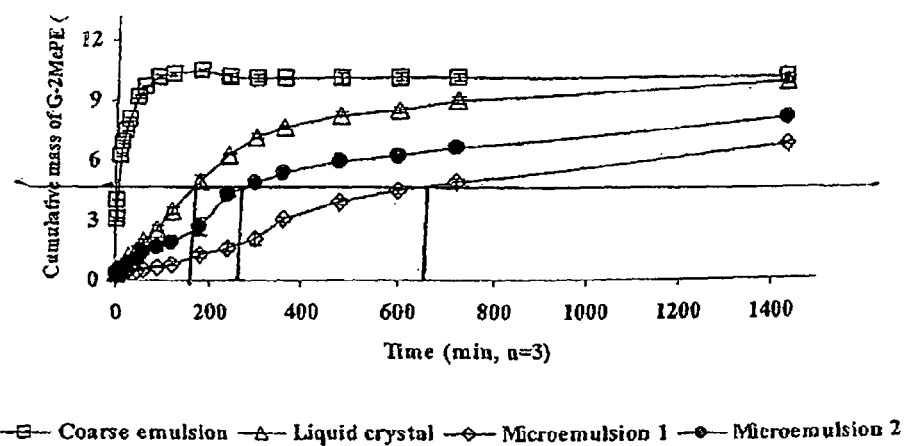
FIG. 13 depicts a graph of profiles of drug released from different formulations of G-2MePE.

The drug release profiles showed that microemulsions and liquid crystal formulations released G-2MePE in a sustained fashion, whereas coarse emulsions unexpectedly released G-2MePE quite rapidly (FIG. 13). MC2 was selected for in vivo studies described in Examples 17 and 18.

Conclusions

We conclude from these studies that all three phase systems can have utility in therapy using G-2MePE. First, microemulsions and liquid crystals can be used in situations in which relatively slow, sustained release of G-2MePE is desired. Next, coarse emulsions can be used when relatively rapid release of G-2MePE is desired. Finally, combinations of either microemulsions plus coarse emulsions or liquid crystals plus coarse emulsions can be desirably use when both rapid release and sustained release of G-2MePE are desired.

Example 15

Bioavailability of Orally Administered G-2MePE

Purpose

The purpose of these studies was to investigate the release of G-2MePE from various delivery systems in vivo.

Methods 7-9 week-old male Wistar rats were used in the experiments. The animals were anaesthetised using a 5% halothane/oxygen mixture and maintained under 3% halothane/oxygen mixture throughout the experiment. A 10 mm incision was made along the mid-line of the neck. Blunt surgical forceps were used to separate the muscles along the right side of the trachea to expose the right-side jugular vein. A polyethylene catheter (OD 1.5 mm, ID 0.6 mm) was introduced into the jugular vein and held in place by sutures. This catheter enabled samples (100 µl) to be collected at selected time points for pharmacokinetic study of G-2MePE. The catheter was filled with heparinized saline (40 IU/ml) to prevent its occlusion by blood clots. Sampling was carried out while the rats were under full general anaesthesia and the rats were euthanized at the end of the experiment.

Sampling from the Cerebral Spinal Fluid

Rats that underwent cerebral spinal fluid (CSF) sampling were anaesthetised with 5% halothane/oxygen. Their heads were placed in a stereotaxic frame. An incision was made across the top of the head and the base of the skull area exposed. CSF was sampled from the cisterna magna using a 29 gauge ultra-fine needle and syringe. The animals were then euthanized using an overdose of pentobarbital (i.p. 180 mg/kg), perfused via the heart with 0.9% saline and tissues were collected for analysis.

In Vivo G-2MePE Pharmacokinetics and Bioavailability

G-2MePE in various formulations was screened to assess their effect on oral bioavailability. The following formulations were tested:

Formulation 1 (G-2MePE dissolved in 35.3 mM taurocholic acid (TA), administered at 10 mg/kg, n=6);

Formulation 2 (G-2MePE formulated into microparticles (MP) and dispersed in 35.3 mM TA, administered at 10 mg/kg, n=6);

Formulation 3 (G-2MePE formulated into MP and dispersed in 35.3 mM TA containing 5 mM bacitracin, administered at 30 mg/kg, n=6);

Formulation 4 (G-2MePE formulated as a microemulsion (MC), administered at 30 mg/kg, n=6);

Formulation 5 (G-2MePE formulated as a MC containing 5 mM bacitracin, administered at 30 mg/kg, n=6);

Formulation 6 (G-2MePE dissolved in 35.3 mM TA to formulate MC, ECA monomer then added to the microemulsion as per Example 13, administered at 30 mg/kg, n=6);

Formulation 7 (G-2MePE dissolved in 35.3 mM TA to formulate MC first, then ECA monomer added, 5 mM bacitracin, administered at 30 mg/kg, n=6). We also tested a control group (n=6) to which G-2MePE dissolved in saline was administered at a dose of 30 mg/kg.

Collected blood samples were centrifuged at 3300 g for 15 min to obtain plasma. Plasma samples were stored at −80° C. Plasma samples were then thawed and analysed by liquid chromatography/mass spectrometry (LCMS). Bioavailability of G-2MePE and its half-lives after oral administration by different formulations were calculated (Table 2 and FIG. 14).

Results

Figure 14:
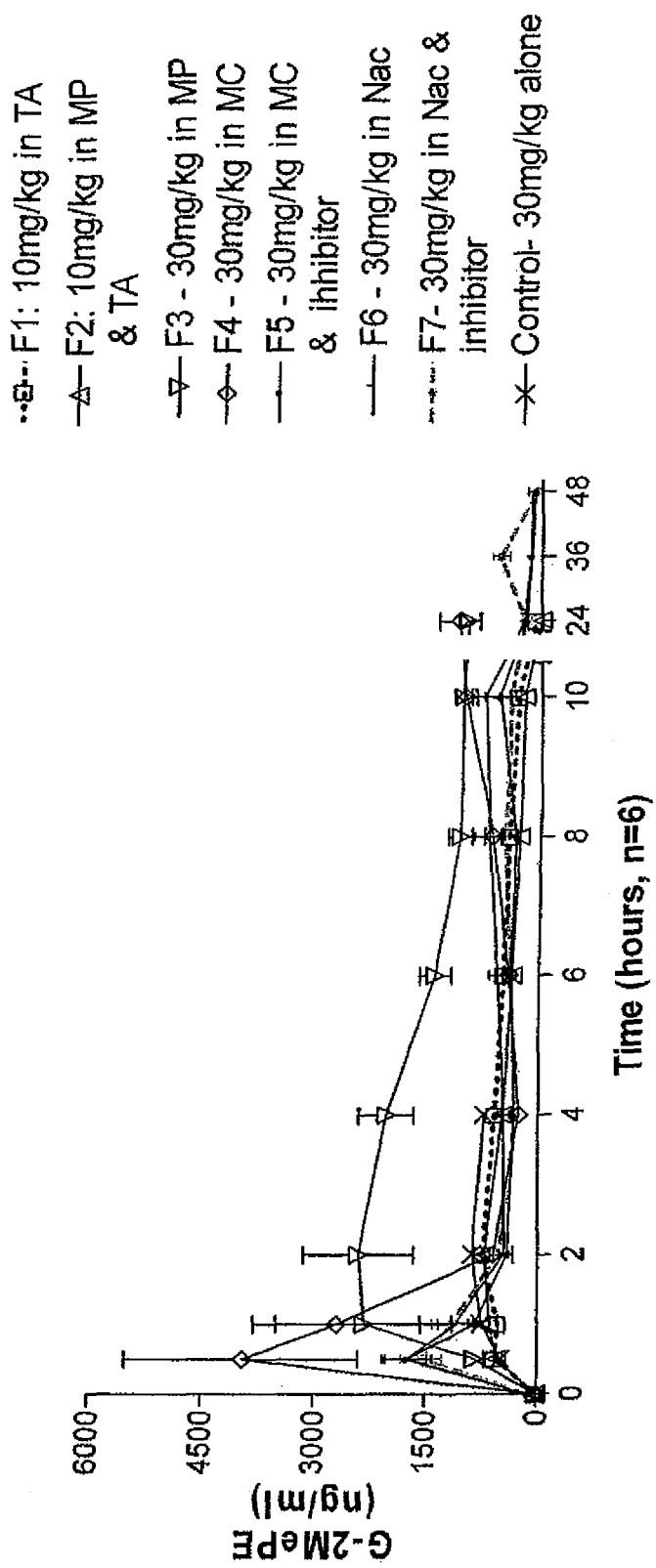
FIG. 14 depicts a graph of pharmacokinetics after oral treatment in rat plasma of several formulations containing G-2MePE.

There was a significant increase of G-2MePE bioavailability when administered in formulations 1-7 compared to G-2MePE administered in saline (P<0.05). Of the seven formulations, G-2MePE in microemulsions and microparticles showed the highest bioavailability (FIG. 14).

TABLE 2

G-2MePE Half-Life and Bioavailability

| Formulation Used | Half life (hours) | Bioavailability % |
|---|---|---|
| Control (30 mg/kg in saline) | 1.67 ± 0.10 | 5.48 ± 0.45 |
| Formulation 1 (10 mg/kg in TA) | 7.86 ± 1.50** | 15.94 ± 1.27** |
| Formulation 2 (10 mg/kg in microparticles) | 4.97 ± 0.24** | 8.74 ± 0.90** |
| Formulation 3 (30 mg/kg in microparticles + bacitracin) | 26.56 ± 5.74** | 41.76 ± 6.52** |
| Formulation 4 (30 mg/kg in microemulsion) | 2.33 ± 0.40 | 32.75 ± 4.58** |
| Formulation 5 (30 mg/kg in microemulsion + bacitracin) | 16.31 ± 1.00** | 19.12 ± 2.53** |
| Formulation 6 (30 mg/kg in microemulsion + ECA) | 13.62 ± 0.48** | 24.15 ± 3.25** |
| Formulation 7 (30 mg/kg in microemulsion + ECA + bacitracin) | 18.18 ± 4.52** | 24.19 ± 4.28** |

**represent P < 0.01.

Conclusions

G-2MePE bioavailability was significantly increased by Formulations 2-7 compared to the aqueous formulation 1. The highest oral bioavailability of G-2MePE was found using microparticles and microemulsions (FIG. 14). Thus, we conclude that emulsions and encapsulated forms of G-2MePE can be effective, orally administered neuroprotective formulations.

Example 16

Endothelin-1 Induced Middle Cerebral Artery Occlusion

Purpose

The purpose of these studies was to determine whether oral G-2MePE can be effective in treating neurodegenerative conditions.

We therefore carried out a series of studies in an art-recognized model of stroke in rats, namely, endothelin-1-induced middle coronary artery occlusion (MCAO). This system is known to mimic neurological and behavioural signs and symptoms of stroke in humans, and therefore, the results obtained are predictive of therapeutic effects in humans with strokes. We measured infarct size and the change in weight between the day of induction of MCAO and day 3 after MCAO induction.

Materials and Methods

Endothelin-1 Induced Middle Cerebral Artery Occlusion

All surgical and experimental procedures carried out in this study had been approved by the University of Auckland Animal Ethics Committee. All efforts were made to minimise any animal suffering and the number of animals used. Adult male Sprague-Dawley rats (280-350 g) were used.

An inhalation anaesthetic (halothane) was co-administered with oxygen to anaesthetise the rats. Initially 5% halothane/oxygen was applied to anaesthetise the animal, and then 2.5% halothane was used to maintain the anaesthesia. Once under anaesthesia, a guide cannula was implanted on the skull of the anaesthetized rats, which was fixed into position with dental cement. Following this implantation, the jugular vein of the animal was also cannulated. Two or three days later, the rats were anaesthetized again as above and subjected to MCAO according to the method of Sharkey and co-workers (Sharkey et al., 1993). This involved placing the head of each rat on a stereotaxic frame and locking it into position. The animals were also placed on a heating pad, which is designed to maintain body temperature within the physiological range for the duration of the surgical procedure.

The hair over the scalp was clipped short with a pair of scissors, sponged and wiped dry with a solution of Betadine® (iodine). Following this, a midline skin incision was made through the scalp to expose the coronal suture line (bregma) of the skull. Then, a small opening was made through the cranial bone using the following co-ordinates: 0.2 mm anterior to and 5.2 mm lateral to bregma. Through a guide cannula, a 28-gauge infusion needle was connected to a 10 µl syringe containing 100 µmol of porcine endothelin-1 (Et-1; Sigma-Aldrich Inc., Saint Louis, Mo., USA) in 3 µl of saline was vertically inserted to a depth of 8.7 mm below the surface of the skull.

To constrict the middle cerebral artery, the solution containing endothelin was injected at a rate of 1 µl per minute for three minutes. After the infusion, the needle was left in place for five more minutes before being withdrawn from the brain. The skin incision was sutured and the animals were moved to a warmed incubator (37° C.) to recover from surgery. Once awake, the animals were then transferred to their cages where they had full access to both food and water. One animal was eliminated from the study on the second day following the induction of MCAO because of an unacceptably high (15%) weight loss.

Histological Procedures

Three days following the drug treatment, the animals were sacrificed using an overdose of sodium pentobarbital and the brains collected for histological evaluation of neuronal survival. The rats were perfused transcardially with 0.9% normal saline followed by 10% formalin. The brain was removed from the skull and stored in the same fixative solution for at least 24 hours. Three 2 mm coronal sections were cut, using a rodent brain matrix (RBM-3000C/RBM-4000C, ASI Instruments, USA). Section A: directly in front of the optical chiasma, section B: directly following section A posterior to the optical chiasma and section C directly following section B. The slices were held in 10% formalin for at least 24 hours, processed in increasing percentage of alcohol and in chloroform and embedded in paraffin for further cutting. At a thickness of 8 µm, coronal sections were cut on a Leica® microtome (Leica Instruments, Nussloch, Germany), mounted onto Polysine™ microscope coated slides (BioLab Scientific, NZ) and stained with thionin-acid fuchsin prior to microscopic evaluation.

Measurement of Weight

Percentage weight change was calculated using the formula: $(w2-w1)/w1 \times 100\%$ where $w2$ is the weight 3 days after endothelin injection and $w1$ is weight at the time of the endothelin injection.

Statistical Analysis

All statistical calculations were carried out using Graph-Pad Prism™ software (Version 3.02, GraphPad Software Inc., San Diego, Calif., USA). Data are presented as mean±S.E.M. and significance was defined at $p<0.05$.

Example 17

Oral Administration of Microemulsion G-2MePE Treats MCAO

Materials and Methods

Endothelin-1 Induced Middle Cerebral Artery Occlusion

The MCAO induction method described in Example 16 above was used. 24 animals were cannulated, all received Et-1 injections, at 2 and then at 4 hours, 12 animals were treated orally with a G-2MePE-containing microemulsion and the remaining 12 animals were treated with vehicle.

Preparation of Microemulsions

Microemulsions containing G-2MePE were prepared according to methods disclosed in Example 12.

G-2MePE Treatment

The rats were administered either miliQ water (n=12) or G-2MePE-containing microemulsion (G-2MePE volume equal to 12 mg/ml of microemulsion) at 2 hours and 4 hours post-MCAO, in a total 80 mg/kg of G-2MePE per rat.

Histological Procedures, Weight Measurements and Statistical Analysis

Histological, weight measurements are as described in Example 16.

Results

Figure 15A:
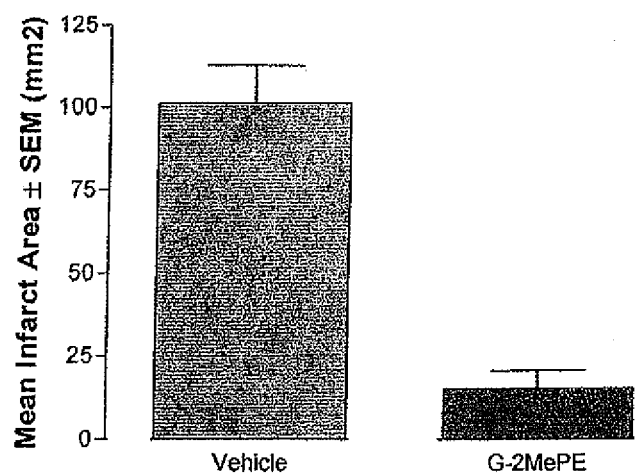
FIG. 15A depicts a graph of effects of a microemulsion containing G-2MePE on infarct size when given orally at 2 and 4 hours after middle cerebral artery occlusion (MCAO) in rats. The total dose of G-2MePE was 80 mg/kg. Vehicle (n=12); G-2MePE (n=11). The difference between vehicle-treated and G-2MePE-treated animals was statistically significant as assessed using an unpaired Student's t-test, p<0.0001.

FIG. 15A shows that the microemulsion formulation of G-2MePE decreased infarct size. The total dose was 80 mg/kg. Vehicle (n=12); G-2MePE (n=11). Unpaired t test, $p<0.0001$.

Figure 15B:
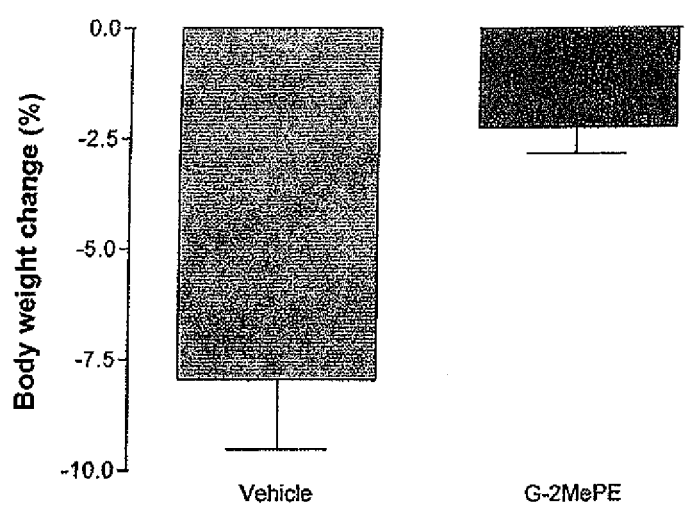
FIG. 15B depicts a graph of effects of a microemulsion containing G-2MePE on change of body weight after middle cerebral artery occlusion. G-2MePE was given orally 2 and 4 hours after MCAO. The total dose was 80 mg/kg. Vehicle (n=12); G-2MePE (n=11). G-2MePE-treated animals lost less weight than vehicle-treated control animals. P=0.0035 by unpaired Student's t-test.

FIG. 15B shows that the microemulsion formulation of G-2MePE diminished the weight loss associated with MCAO. Vehicle (n=12); G-2MePE (n=11). G-2MePE-treated animals lost less weight than vehicle-treated control animals. P=0.0035.

Conclusion

We conclude from this study that microemulsions of G-2MePE can be effective treatments for MCAO in rats after oral administration. Because this experimental system is predictive of effects observed in human beings with strokes, we also conclude that microemulsions of G-2MePE can be orally active to treat humans suffering from strokes.

Example 18

G-2MePE Microemulsion: Oral Dose Response Study

Purpose

The purpose of this study was to establish the dose response curve or the microemulsion containing 6 mg of G-2MePE per 1 ml of microemulsion.

Materials and Methods

Endothelin-1 Induced Middle Cerebral Artery Occlusion

We used the MCAO induction method described in Example 16 above. 39 animals were cannulated, all received Et-1 injections, 7 animals died or were sacrificed before the end of the post-MCAO 3-day survival period.

Preparation of Microemulsions

Microemulsions were prepared as described in Example 12.

G-2MePE Treatment

Animals were treated orally 3 hours after MCAO was induced. Animals were treated with either the microemulsion containing 6 mg G-2MePE/ml or miliQ water as a vehicle. The drug was delivered at a volume adjusted for body weight in order to deliver 15, 30 or 60 mg/kg.

Histological Procedures, Weight Measurements and Statistical Analysis

Determination of infarct size, body weight and statistical analysis were carried out as described in Example 16.

Results

Figure 16A:
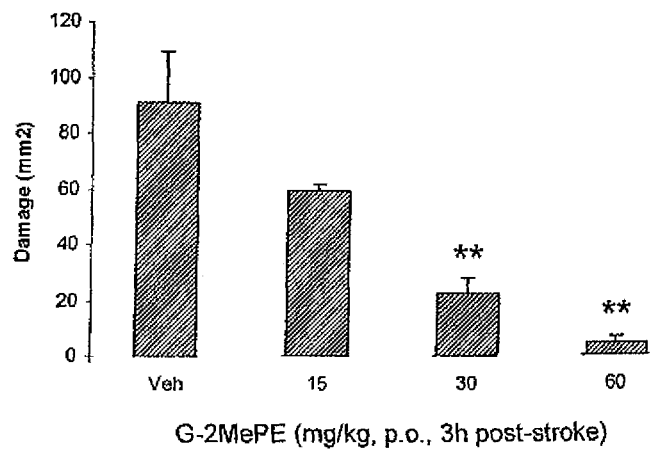
FIG. 16A depicts a graph of effects of microemulsions containing different doses of G-2MePE on infarct size when given orally 3 hours after MCAO. Data were analysed using One-way ANOVA with Dunnett's post-hoc test. Data are presented as means±SEM. Vehicle (n=9), 15 mg/kg (n=8), 30 mg/kg (n=8), 60 mg/kg (n=7). ★, p≦0.05; ★★, p≦0.01; ★★★, p≦0.001.
Figure 16B:
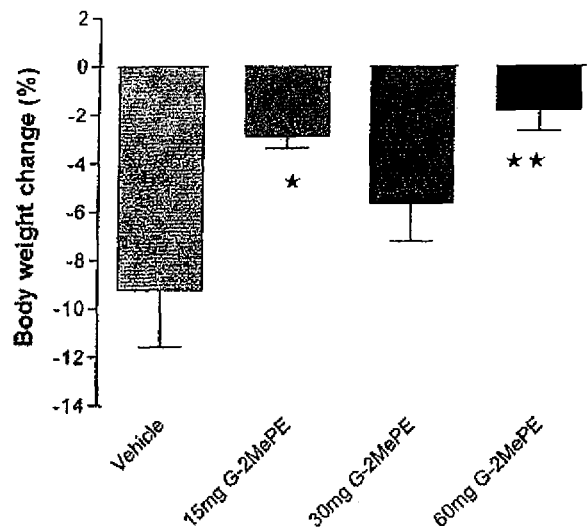
FIG. 16B depicts a graph of effects of microemulsions containing different doses of G-2MePE on body weight change when given orally 3 hours after MCAO. Data were analysed using One-way ANOVA with Dunnett's post test. Data are presented as means±SEM. Vehicle (n=8), 15 mg/kg (n=7), 30 mg/kg (n=7), 60 mg/kg (n=7) ★, p≦0.05; ★★, p≦0.01; ★★★, p≦0.001.

Orally administered G-2MePE caused a dose-dependent decrease in cerebral infarct size. At the highest dose of G-2MePE, the degree of inhibition was 94.5% (FIG. 16A). We also found that orally administered G-2MePE reduced the weight loss associated with MCAO (FIG. 16B).

Conclusions

We conclude that orally administered microemulsion formulations containing G-2MePE can be effective in reversing deleterious effects of strokes in rats. We also conclude that other formulations of G-2MePE of this invention can be effective in reversing deleterious effects of MCAO. Further, because the MCAO system studied here is reasonably predictive of therapeutic effects observed in humans, we conclude that formulations of this invention containing G-2MePE can be effective in treating human beings with chronic and/or acute neurological disorders, including strokes or other cerebral injuries and diseases, including hypoxia/ischemia, Alzheimer's disease, Parkinson's disease and other chronic neurodegenerative conditions. Finally, we also conclude that formulations of G-2MePE of this invention can be useful in treating neurodegenerative effects associated with acute injuries, including traumatic brain injury, coronary infarcts, acute hypoxia or ischemia or other disorders characterized by neural degeneration or cell death.

Example 19

Oral Administration of Aqueous Formulation of G-2MePE

Purpose

To provide a basis for comparing efficacies of microemulsions to aqueous formulations containing G-2MePE, we performed studies comparable to those described above, but using G-2MePE dissolved in saline instead of microemulsion formulations.

Materials and Methods

Endothelin-1 Induced Middle Cerebral Artery Occlusion

The MCAO induction method described in Example 16 above was used.

G-2MePE Treatment

Lyophilised G-2MePE was dissolved in water at 10 mg/ml. At five hours post Et-1 injection, 2 ml of G-2MePE formulation, i.e. 60 mg/kg (n=11) or 2 ml milliQ water (vehicle treated group, n=13) were administered to each animal by oral gavage 3 h post MCAo.

Histological Procedures, Weight Measurements and Statistical Analysis

Histological methods, weight measurements and statistical analyses were performed as described in Example 16.

Results

Effect of Aqueous Solutions of G-2MePE on Infarct Size

Figure 17A:
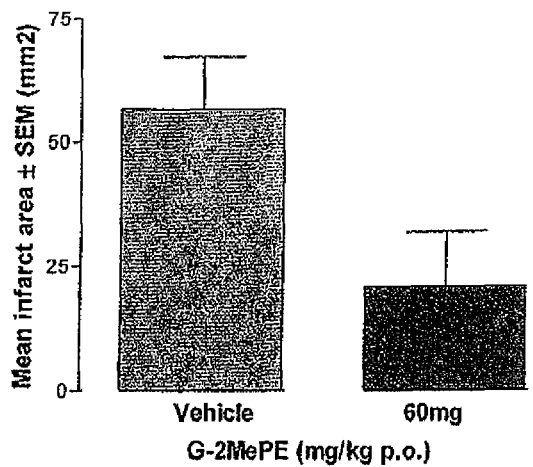
FIG. 17A depicts a graph of effects of oral administration of aqueous solutions of G-2MePE or vehicle treatment on area of infarct (in mm$^2$) following injection of endothelin-1 (Et-1) to produce MCAO. Three hours after Et-1 injection, G-2MePE (60 mg/kg) (n=11) or vehicle (milliQ water) (n=13) were administered orally to rats. Data are presented as mean±S.E.M. and significance was defined at p<0.05.

Oral administration of aqueous solutions of G-2MePE (60 mg/kg) significantly reduced the area of the infarct compared to the vehicle-treated group (n=13, *$P<0.05$) (FIG. 17A). The inhibition produced by aqueous G-2MePE was about 63% of the vehicle-treated animals (FIG. 17A). In contrast, the inhibition produced by the microemulsion formulation of G-2MePE greater than that produced by the aqueous formulation (see FIG. 16A; i.e., 94% inhibition).

Effect of Aqueous Solutions of G-2MePE on Percentage Weight Change

Figure 17B:
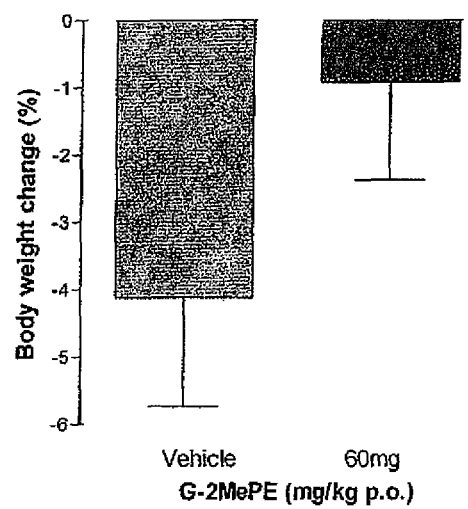
FIG. 17B depicts a graph of effects of oral administration of aqueous solutions of G-2MePE or vehicle treatment on the change in weight following Et-1-induced MCAO in rats.

Oral administration of aqueous solutions of G-2MePE (60 mg/kg) reduced the weight loss in animals with MCAO by about ¾, although the effect was not statistically significant ($p<0.2$) (FIG. 17B). However, in animals treated with G-2MePE, the weight change was not statistically different from zero.

Conclusions

We conclude from these studies that emulsion formulations of G-2MePE can improve bioavailability of the drug compared to simple aqueous solutions, and can result in sustained concentrations of the drug in animals, thereby making these formulations useful for in vivo use in human beings and other animals.

We surprisingly found that the degree of neuroprotection afforded by orally delivered microemulsions (95%) was nearly complete as measured by infarct size. This unexpectedly larger effect compared to orally administered aqueous solutions of G-2MePE (63%) means that formulations of G-2MePE of this invention can be of advantage over aqueous preparations. Thus, encapsulated or microemulsion preparations of G-2MePE can be useful in treating a variety of conditions characterized by neurodegeneration, including stroke, hypoxia/ischemia, TBI, CABG and chronic neurodegenerative conditions.

Example 20

Comparison of Intravenous and Orally Administered G-2MePE

Purpose

The purpose of this study was to compare the effects of intravenous administration of an aqueous preparation of G-2MePE with those observed in the previous study using G-2MePE in microemulsion formulations (FIG. 16A).

Methods

We used animals prepared as in Example 16 for the endothelin-1-induced MCAO. However, here, the G-2MePE was delivered intravenously as an aqueous solution in doses of 1.2, 12 and 120 mg/kg administered over a 4 hour period of time after MCAO.

12 animals were treated with vehicle (saline) and 11 animals were treated with aqueous solutions of G-2MePE (i.v.).

Results

Figure 18:
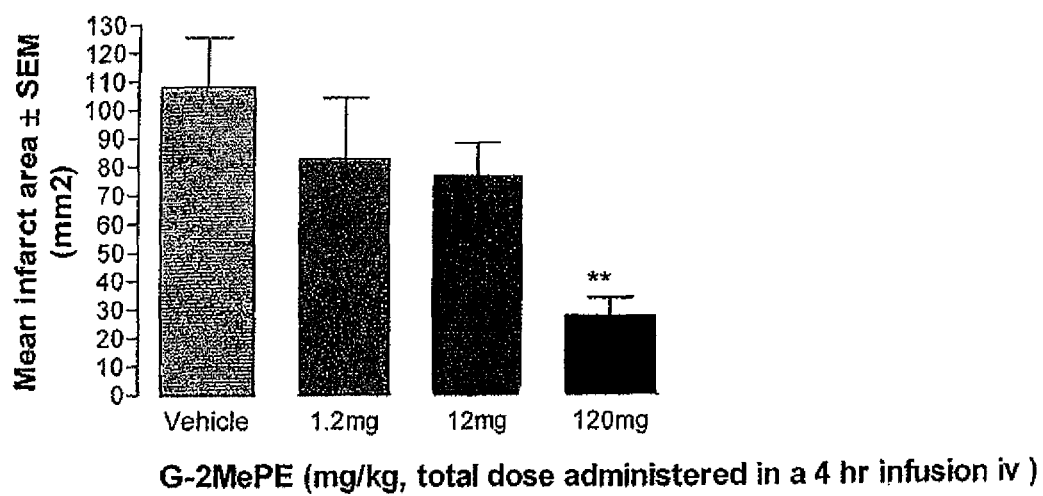
FIG. 18 depicts a graph of effects of intravenously administered aqueous solutions of G-2MePE on endothelin-1-induced MCAO.

Results of this study are shown in FIG. 18, which is a graph depicting the mean infarct area observed after endothelin-1-induced MCAO. Intravenously administered aqueous solutions of G-2MePE caused a dose-dependent decrease in infarct size, with the largest effect observed at a total dose of 120 mg/kg G-2MePE. The amount of neuroprotection provided by this dose of aqueous G-2MePE was about 74.4% compared to vehicle-treated control animals. Data are presented as mean±SEM; ** P<0.01 using ANOVA and Dunnett's post hoc test.

We surprisingly found that orally administered emulsion formulations of G-2MePE at ½ of this dose (i.e., 60 mg/kg) produced substantially greater inhibition of infarct size (94.5% inhibition) than was observed for the aqueous solutions of G-2MePE. This result was completely unexpected based on the prior understanding of effects of G-2MePE.

We conclude from these studies that our novel formulations of G-2MePE can be beneficial for in vivo oral administration to animals including human beings to treat neurodegeneration resulting from acute and or chronic neurological disorders. Thus, these formulations provide advances in therapy for dealing with heretofore difficult to treat neurololical diseases and injuries.

It can be appreciated that the descriptions, examples and figures herein are used to illustrate specific embodiments of this invention. Persons of ordinary skill in the art can use the disclosures and teachings of this application and can make obvious variations, modifications and alternative embodiments without departing from the scope of this invention. All of these variations, modifications and alternative embodiments are considered part of this invention.

We claim:

1. A composition comprising:
Glycyl-2-methyl-prolyl-glutamate (G-2MePE) in a water-in-lipid emulsion; said lipid comprising a carboxylic acid.

2. The composition of claim 1, wherein said carboxylic acid has a chain length of $C_{16}$-$C_{22}$ with up to three unsaturated bonds.

3. The composition of claim 1, said lipid comprising a saturated straight chain acid selected from the group consisting of n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, and melissic acid.

4. The composition of claim 1, said carboxylic acid comprising an unsaturated monoolefinic straight chain monocarboxylic acid selected from the group consisting of oleic acid, gadoleic acid, and erucic acid.

5. The composition of claim 1, said lipid comprising an unsaturated (polyolefinic) straight chain monocarboxylic acid selected from the group consisting of linoleic acid, ricinoleic acid, linolenic acid, arachidonic acid, and behenolic acid.

6. The composition of claim 1, said lipid comprising diacetyl tartaric acid.

7. The composition of claim 2, said lipid comprising a long chain ($C_{16}$-$C_{22}$) carboxylic acid ester selected from the group consisting of glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated monoglycerides; mixtures of propylene glycol monoesters, distilled monoglycerides, sodium steroyl lactylate and silicon dioxide; d-alpha tocopherol, polyethylene glycol 1000 succinate; calcium stearoyl lactylate; ethoxylated mono- and di-glycerides; lactated mono- and di-glycerides; lactylate carboxylic acid ester of glycerol and propylene glycol; lactylic esters; polyglycerol esters of $C_{16}$-$C_{22}$ carboxylic acids, propylene glycol mono- and di-esters of $C_{16}$-$C_{22}$ carboxylic acids; sodium stearoyl lactylate; sorbitan monostearate; sorbitan monooleate; other sorbitan esters of $C_{16}$-$C_{22}$ carboxylic acids; succinylated monoglycerides; stearyl monoglyceryl citrate; stearyl heptanoate; cetyl esters of waxes; stearyl octanoate; $C_{10}$-$C_{30}$ cholesterol/lavosterol esters; and sucrose $C_{16}$-$C_{22}$ carboxylic acid esters.

8. The composition of claim 2, said $C_{16}$-$C_{22}$ carboxylic acid selected from the group consisting of stearates, palmitates, ricinoleates, oleates, behenates, ricinolenates, myristates, laurates, caprylates, and caproates.

9. The composition of claim 1, said emulsion comprising an alcohol selected from a hydroxyl form of a carboxylic acid of claim 7, or a strearyl alcohol.

10. A pharmaceutical composition, comprising:
glycyl-2-methyl prolyl glutamate (G-2MePE); and
a peptide conjugating agent.

11. The pharmaceutical composition of claim 10, said peptide conjugating agent being a solid or a semisolid.

12. The pharmaceutical composition of claim 11, said peptide conjugating agent being a carrier molecule.

13. The pharmaceutical composition of claim 10, said composition being a polymer containing said G-2MePE peptide and said conjugating agent being ethyl 2-cyanoacrylate.

14. The pharmaceutical composition of claim 12, said composition being freeze dried.

15. The composition of claim 1, said G-2MePE being Glycyl-2-methyl-L-prolyl-L-glutamate.

16. The composition of claim 15, wherein said carboxylic acid has a chain length of $C_{16}$-$C_{22}$ with up to three unsaturated bonds.

17. The composition of claim 15, said lipid comprising a saturated straight chain acid selected from the group consisting of n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, and melissic acid.

18. The composition of claim 15, said carboxylic acid comprising an unsaturated monoolefinic straight chain monocarboxylic acid selected from the group consisting of oleic acid, gadoleic acid, and erucic acid.

19. The composition of claim 15, said lipid comprising an unsaturated (polyolefinic) straight chain monocarboxylic acid selected from the group consisting of linoleic acid, ricinoleic acid, linolenic acid, arachidonic acid, and behenolic acid.

20. The composition of claim 15, said lipid comprising diacetyl tartaric acid.

21. The composition of claim 16, said lipid comprising a long chain ($C_{16}$-$C_{22}$) carboxylic acid ester selected from the group consisting of glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated monoglycerides; mixtures of propylene glycol monoesters, distilled monoglycerides, sodium steroyl lactylate and silicon dioxide; d-alpha tocopherol, polyethylene glycol 1000 succinate; calcium stearoyl lactylate;

ethoxylated mono- and di-glycerides; lactated mono- and di-glycerides; lactylate carboxylic acid ester of glycerol and propylene glycol; lactylic esters; polyglycerol esters of $C_{16}$-$C_{22}$ carboxylic acids, propylene glycol mono- and di-esters of $C_{16}$-$C_{22}$ carboxylic acids; sodium stearoyl lactylate; sorbitan monostearate; sorbitan monooleate; other sorbitan esters of $C_{16}$-$C_{22}$ carboxylic acids; succinylated monoglycerides; stearyl monoglyceryl citrate; stearyl heptanoate; cetyl esters of waxes; stearyl octanoate; $C_{10}$-$C_{30}$ cholesterol/lavosterol esters; and sucrose $C_{16}$-$C_{22}$ carboxylic acid esters.

22. The composition of claim 16, said $C_{16}$-$C_{22}$ carboxylic acid selected from the group consisting of stearates, palmitates, ricinoleates, oleates, behenates, ricinolenates, myristates, laurates, caprylates, and caproates.

23. The composition of claim 15, said emulsion comprising an alcohol selected from a hydroxyl form of a a carboxylic acid ester selected from the group consisting of glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated monoglycerides; mixtures of propylene glycol monoesters, distilled monoglycerides, sodium steroyl lactylate and silicon dioxide; d-alpha tocopherol, polyethylene glycol 1000 succinate; calcium stearoyl lactylate; ethoxylated mono- and di-glycerides; lactated mono- and di-glycerides; lactylate carboxylic acid ester of glycerol and propylene glycol; lactylic esters; polyglycerol esters of $C_{16}$-$C_{22}$ carboxylic acids, propylene glycol mono- and di-esters of $C_{16}$-$C_{22}$ carboxylic acids; sodium stearoyl lactylate; sorbitan monostearate; sorbitan monooleate; other sorbitan esters of $C_{16}$-$C_{22}$ carboxylic acids; succinylated monoglycerides; stearyl monoglyceryl citrate; stearyl heptanoate; cetyl esters of waxes; stearyl octanoate; $C_{10}$-$C_{30}$ cholesterol/lavosterol esters; and sucrose $C_{16}$-$C_{22}$ carboxylic acid esters, or a strearyl alcohol.

24. The composition of claim 15, further comprising a peptide conjugating agent.

25. The composition of claim 24, said peptide conjugating agent being a solid or a semisolid.

26. The composition of claim 24, said peptide conjugating agent being a carrier molecule.

27. The composition of claim 24, said composition being a polymer containing said Glycyl-2-methyl-L-prolyl-L-glutamate peptide and said conjugating agent being ethyl 2-cyanoacrylate.

28. The composition of claim 24, said composition being freeze dried.

* * * * *